x

US010564160B2

(12) United States Patent
Dosenovic et al.

(10) Patent No.: US 10,564,160 B2
(45) Date of Patent: Feb. 18, 2020

(54) ANTIBODY-SECRETING CELL ASSAY

(75) Inventors: Pia Dosenovic, Stockholm (SE); Gunilla Karlsson Hedestam, Stockholm (SE); Richard Wyatt, La Jolla, CA (US); Staffan Paulie, Nacka Strand (SE)

(73) Assignee: MABTECH AB, Nacka Strand (SE)

( * ) Notice: Subject to any disclaimer, the term of this patent is extended or adjusted under 35 U.S.C. 154(b) by 203 days.

(21) Appl. No.: 13/061,085

(22) PCT Filed: Aug. 28, 2009

(86) PCT No.: PCT/EP2009/006274
§ 371 (c)(1),
(2), (4) Date: Jun. 20, 2011

(87) PCT Pub. No.: WO2010/022980
PCT Pub. Date: Mar. 4, 2010

(65) Prior Publication Data
US 2011/0244477 A1    Oct. 6, 2011

(30) Foreign Application Priority Data

Aug. 28, 2008    (GB) .................................. 0815675.4

(51) Int. Cl.
*G01N 33/569*    (2006.01)
(52) U.S. Cl.
CPC .............................. *G01N 33/56972* (2013.01)
(58) Field of Classification Search
None
See application file for complete search history.

(56) References Cited

U.S. PATENT DOCUMENTS

| | | | |
|---|---|---|---|
| 4,273,756 A | 6/1981 | Ling et al. | |
| 7,105,655 B2 | 9/2006 | Sodroski et al. | |
| 2003/0026782 A1* | 2/2003 | Krieg | A61K 31/4706 424/93.2 |
| 2003/0027205 A1* | 2/2003 | Martinez | G01N 33/543 13 435/6.16 |
| 2005/0079557 A1 | 4/2005 | Vendrell et al. | |
| 2005/0220817 A1 | 10/2005 | Sodroski et al. | |
| 2008/0038755 A1 | 2/2008 | Kauvar et al. | |

FOREIGN PATENT DOCUMENTS

| | | | |
|---|---|---|---|
| EP | 0346119 A2 | | 12/1989 |
| FR | 2556840 A1 | | 6/1985 |
| WO | WO 90/04182 A1 | | 4/1990 |
| WO | WO 91/05260 A1 | | 4/1991 |
| WO | WO 94/24560 A1 | | 10/1994 |
| WO | WO 98/16829 A1 | | 4/1998 |
| WO | WO 1998/21581 | * | 5/1998 |
| WO | WO 01/19958 A2 | | 3/2001 |
| WO | WO 03/076942 A2 | | 9/2003 |
| WO | WO 2007/003041 | * | 1/2007 |
| WO | WO 08/029251 A2 | | 3/2008 |

OTHER PUBLICATIONS

Sissoeff et al., Journal of General Virology, 2005, 86:2543-2552.*
Vendrell et al., Journal of Virology, 1992, 30(8):2200-2203.*
Binley et al., "A recombinant human immunodeficiency virus type 1 envelope glycoprotein complex stabilized by an intermolecular disulfide bond between the gp120 and gp41 subunits is an antigenic mimic of the trimeric virion-associated structure," *Journal of Virology* 74:627-643 (2000).
Bromage et al., "The third dimension of ELISPOTs:Quantifying antibody secretion from individual plasma cells," *Journal of Immunological Methods* 346:75-79 (2009).
Cox et al., "An early humoral immune response in peripheral blood following parenteral inactivated influenza vaccination," *Vaccine* 12:993-999 (1994).
Dosenovic et al., "Selective expansion of HIV-1 envelope glycoprotein-specific B cell subsets recognizing distinct structural elements following immunization," *The Journal of Immunology* 183:3373-3382 (2009).
Fondere et al., "Detection of peripheral HIV-1-specific memory B cells in patients untreated or receiving highly active antiretroviral therapy," *AIDS* 17:2323-2330 (2003).
Frossard et al., "Antigen-specific secretory IgA antibodies in the gut are decreased in a mouse model of food allergy," *The Journal of Allergy and Clinical Immunology* 114:377-382 (2004).
Gazagne et al., "A fluorospot assay to detect single T lymphocytes simultaneously producing multiple cytokines," *Journal of Immunological Methods* 283:91-98 (2003).
Gazagne et al., "Fluorospot Assay," *Methods in Molecular Biology, vol. 302: Handbook of ELISPOT:Methods and Protocols*, (Kalyuzhny, ed.) Humana Press:Totowa, NJ, 289-295, 1996.
Kim et al., "Comparison of HIV type 1 ADA gp120 monomers versus gp140 trimers as immunogens for the induction of neutralizing antibodies," *AIDS Research and Human Retroviruses* 21:58-67 (2005).
Li et al., "Characterization of antibody responses elicited by human immunodeficiency virus type 1 primary isolate trimeric and monomeric envelope glycoproteins in selected adjuvants," *Journal of Virology* 80:1414-1426 (2006).
Lycke et al., "Measurement of Immunoglobulin Synthesis Using the ELISPOT Assay," *Current Protocols in Immunology*, (Coligan, ed.) Wiley & Sons: Hoboken NJ, Ch. 7, Unit 7.14:1-9, 2001.
Nielsen et al., "Detection of immunoglobulin G antibodies to cytomegalovirus antigens by antibody capture enzyme-linked immunosorbent assay," *Journal of Clinical Microbiology*, 24:998-1003 (1986).

(Continued)

*Primary Examiner* — Nicole Kinsey White
(74) *Attorney, Agent, or Firm* — Clark & Elbing LLP

(57) ABSTRACT

An improved assay is described where a surface is provided with immobilized anti-Ig antibodies rather than antigen and where specific antibody-secreting cells (ASC) are detected using soluble antigen probes containing one of several possible labels. The method gives improved sensitivity with less background and is also more representative because antigen binding does not employ immobilized antigen. The assay is particularly effective for measuring antibody secreting cells against HIV, for determining whether an infection is acute as opposed to old or latent, for mapping epitopes and for measuring for ASCs against different antigens in the same reaction.

24 Claims, 16 Drawing Sheets
Specification includes a Sequence Listing.

(56) References Cited

OTHER PUBLICATIONS

Nesheim et al., "Diagnosis of human immunodeficiency virus infection by enzyme-linked immunospot assays in a prospectively followed cohort of infants of human immunodeficiency virus-seropositive women," *The Pediatric Infectious Disease Journal* 11:635-639 (1992).
Poussin et al., "Capture-ELISA: a new assay for the detection of immunoglobulin M isotype antibodies using *Chlamydia trachomatis* antigen," *Journal of Immunological Methods*, 204:1-12 (1997).
Rebhahn et al., "Automated analysis of two- and three-color fluorescent Elispot (Fluorospot) assays for cytokine secretion," *Computer Methods and Programs in Biomedicine* 92:54-65 (2008).
Sanders et al., "Stabilization of the soluble, cleaved, trimeric form of the envelope glycoprotein complex of human immunodeficiency virus type 1," *Journal of Virology* 76:8875-8889 (2002).
Schmitz et al., "Detection of specific immunoglobulin M antibody to different flaviviruses by use of enzyme-labeled antigens," *Journal of Clinical Microbiology* 19:664-667 (1984).
Srivastava et al., "Purification, characterization, and immunogenicity of a soluble trimeric envelope protein containing a partial deletion of the V2 loop derived from SF162, an R5-tropic human immunodeficiency virus type 1 isolate," *Journal of Virology* 77:11244-11259 (2003).
Tan et al., "Active immunotherapy of tumors with a recombinant xenogeneic endoglin as a model antigen," *European Journal of Immunology* 34:2012-2021 (2004).
Tuaillon et al., "Detection of memory B lymphocytes specific to hepatitis B virus (HBV) surface antigen (HBsAg) from HBsAg-vaccinated or HBV-immunized subjects by ELISPOT assay," *Journal of Immunological Methods* 315:144-152 (2006).
Tuaillon et al., "Long-term persistence of memory B cells specific for hepatitis B surface antigen in HIV-1-infected patients," *AIDS* 21:2343-2345 (2007).
Vos et al., "Substantially increased sensitivity of the spot-ELISA for the detection of anti-insulin antibody-secreting cells using a capture antibody and enzyme-conjugated insulin," *Journal of Immunological Methods* 126:89-94 (1990).

Yang et al., "Characterization of stable, soluble trimers containing complete ectodomains of human immunodeficiency virus type 1 envelope glycoproteins," *Journal of Virology* 74:5716-5725 (2000).
Yang et al., "Improved elicitation of neutralizing antibodies against primary human immunodeficiency viruses by soluble stabilized envelope glycoprotein trimers," *Journal of Virology* 75:1165-1171 (2001).
Yang et al., "Highly stable trimers formed by human immunodeficiency virus type 1 envelope glycoproteins fused with the trimeric motif of T4 bacteriophage fibritin," *Journal of Virology*, 76:4634-4642 (2002).
Zouali et al., "Quantitative clonal analysis of the B cell repertoire in human lupus," *Cellular Immunology* 133:161-177 (1991).
UK Intellectual Property Office Search Report for Patent Application No. GB0815675.4, dated Dec. 16, 2008 (2 pages).
International Search Report for PCT/EP2009/006274, dated Feb. 5, 2010 (10 pages).
International Preliminary Report on Patentability PCT/EP2009/006274, including Written Opinion, dated Mar. 3, 2011 (14 pages).
Morris et al., "HIV-1 antigen-specific and -nonspecific B cell responses are sensitive to combination antiretroviral therapy," *Journal of Experimental Medicine* 188:233-245 (1998).
International Preliminary Report on Patentability PCT/EP2009/006274, including Written Opinion, dated Mar. 1, 2011 (14 pages).
Kesa et al., "Comparison of ELISpot and FluoroSpot in the Analysis of Swine Flu-Specific IgG and IgA Secretion by in Vivo Activated Human B Cells," *Cells* 1:27-34 (2012).
Hadjilaou et al., "Single-Cell Analysis of B Cell/Antibody Cross-Reactivity Using a Novel Multicolor FluoroSpot Assay," *J Immunol.* 195(7):3490-6 (2015).
Jahnmatz et al., "An antigen-specific, four-color, B-cell FluoroSpot assay utilizing tagged antigens for detection," *J Immunol Methods.* 433:23-30 (2016).
Lucia et al., "Preformed circulating HLA-specific memory B cells predict high risk of humoral rejection in kidney transplantation," *Kidney Int.* 88(4):874-87 (2015) (14 pages).

* cited by examiner

Conventional ELISpot　　　Alternative ELISpot

IgE

IL-2

| Anti-IFN-γ cells: | 200 | 200 |
| Anti-IgE cells: | 0 | 100.000 |

Conventional ELISpot    Alternative ELISpot

ALP
BCIP/NBT

No. of spots: 53    No. of spots: 113

HRP
TMB

No. of spots: 44    No. of spots: 114

| Conventional ELISpot | Alternative ELISpot |

Before vaccination

After vaccination

| Conventional ELISpot | Alternative ELISpot | a)

(F)

b)

a)
- For immunization:
gp140-F

- For probing:
1. gp140-F-biotin ("wt" gp140 protein) 
2. gp120-F-biotin (gp120 trimers) 
3. gp120-F-ΔV1/2-biotin (V12 deleted) 
4. gp120-F-ΔV3-biotin (V3 deleted) 
5. gp120-F- ΔV1/2/3-biotin (V1-3 deleted) 
6. gp120-biotin (monomers) 
7. gp120-denat-biotin (denatured gp120) 
8. B-gal-Biotin (control)

b)

a)

b)

ANTIBODY-SECRETING CELL ASSAY

CROSS-REFERENCE TO RELATED APPLICATIONS

This application is the U.S. national stage filing under 35 U.S.C. § 371 of International Application No. PCT/EP2009/006274, filed Aug. 28, 2009, which claims benefit of British Patent Application No. GB 0815675.4, filed Aug. 28, 2008.

FIELD OF THE INVENTION

The present invention relates to an antibody secreting cell (ASC) assay and to diagnostic methods and vaccine research methods using the assay. The assay, may, in particular, be used to detect B cells.

BACKGROUND TO THE INVENTION

Various assays exist for measuring Antibody Secreting Cells (ASCs). One such assay is the antibody-secreting cell ELISpot which was first described in 1983 and is a method which enables detection of antibody secreting cells at the single cell level. The ELISpot can either be performed so that all antibody secreting cells or only the cells secreting antibodies specific for a particular antigen are detected. By using specific reagents, one can also restrict the detection to a certain immunoglobulin (Ig) isotype (for example, IgG, IgA or IgE) or IgG subclass (for example, IgG1, IgG2 or IgG3).

For the antigen-specific ASC ELISpot, the antigens to be tested are coated onto the membrane of ELISpot plates to which the ASCs are added and incubated for various time spans (from a few hours to several days). During this time antibodies secreted from individual cells may bind to the coated antigen at the site of the secreting cell. After removing the cells, the specifically and locally bound antibodies are visualized by the addition of labelled (for example with an enzyme or biotin) anti-Ig antibodies. If using biotin, an additional step with enzyme-labeled Streptavidin or avidin is required before finally developing the plates by the addition of a precipitating substrate. Each spot observed on the ELISpot plate corresponds to one cell producing the correct antibody and the spots can be counted either manually under a microscope or in an ELISpot reader.

The ELISpot assay may be used to detect all antibody-secreting cells regardless of their specificity by coating the ELISpot plates with anti-Ig antibodies and then visualizing the bound antibodies using labelled anti-Ig antibodies in the same way as for the antigen-specific ASC ELISpot. When the total Ig ASC ELISpot is carried out in parallel to the antigen-specific ASC cell ELISpot as a positive control, the frequency of specific ASCs can be calculated from the number of spots observed in each assay.

A negative control with uncoated wells may also be used. No spots should be observed in these wells. However, the negative control may not always be negative. Spots occurring in negative control wells may represent non-specifically binding "sticky" antibodies or antibodies reactive to proteins, such as BSA or serum used for blocking the ELISpot plates.

The conventional antigen-specific ASC ELISpot assay described above has several other disadvantages. For example, to obtain good quality spots, a large amount of the antigen has to be used to coat the plates and the scarcity and cost of many antigens may be limiting in many situations. Further, due to the uncontrollability of binding and immobilization of antigen to the ELISpot plate, relevant antigen epitopes can become unavailable for antibody binding, either through "masking" (i.e. the epitope is involved in the binding to the plate and thereby made inaccessible) or denaturing of the conformational structure of the protein when immobilized to the plate. In addition, some proteins (particularly smaller peptides) as well as other substances (e.g. carbohydrates and lipids) may not bind efficiently to the ELISpot plate.

The antigen-specific ASC ELISpot can also only readily be carried out to test one antigen in each well of the ELISpot plate as it is not possible to distinguish and separately count the cells producing antibodies to the different antigens.

SUMMARY OF THE INVENTION

The present inventors have produced a new antigen-specific ASC assay protocol by coating the wells with anti-Ig antibodies instead of coating wells with the antigen. The cells are then added and incubated. Antibodies produced by all of the antibody secreting cells will be captured at the site of the producing cells. The captured antibodies can then be visualized by adding a labelled antigen so that only cells producing antibodies for that particular antigen are detected.

The present inventors have tested this alternative approach in several different systems and have surprisingly found that it gives significantly better results compared with the conventional ELISpot technique in which the antigen is immobilized on the membrane. The assay may be performed as an ELISpot assay, but with immobilised anti-Ig antibodies, rather than antigen, followed by labelled antigen. In a preferred instance, the assay may employ fluorescence detection, particularly being a fluorospot type assay, but where immobilized anti-Ig antibodies are employed.

The inventors have found that the alternative ASC assay is more sensitive than the conventional assay. When ELISpot plates were coated with anti-Ig antibodies and captured antibodies produced by ASCs were detected using a labelled antigen, the spots observed were more distinct and easier to evaluate than the spots observed in the conventional ELISpot assay. More spots were also observed. Thus, the assay of the invention represents an advance over the conventional ACS ELISpot assay.

In addition, the inventors found that whilst significant numbers of background spots were seen with the conventional ELISpot assay due to binding of generally "sticky" antibodies or antibodies reactive to proteins used for "blocking" the ELISpot plates, no background spots were observed using the alternative technique. Even low frequency background spots may cause significant problems considering that the specific responses can typically occur at similarly low frequencies and so the absence of background spots in the alternative assay is a particular advantage, In particular, avoidance of background spots facilitates the evaluation and increases the sensitivity of the test. This may also mean that it may not be necessary to include a negative control. Such reduction of the number of test wells, and thereby also a need for fewer cells, may be an important advantage in a diagnostic test particularly where samples are in short supply, such as samples from children, infants and babies where only small samples may be obtained and it may be undesirable to take multiple samples.

From a practical viewpoint, the new assay technique has the additional advantages of requiring significantly less antigen that a conventional ELISpot and enabling potential negative effects on antigenic agents to be better controlled, due to the use of labelled antigen to detect bound antibodies, rather than using immobilized antigen as a capture reagent.

A further advantage compared to conventional methods is that the binding of the antigen in solution is a better way to investigate an antibody's binding to its antigen. For instance when making monoclonal antibodies from hybridomas and using ELISA with coated antigen as the screening for positive clones, quite often positive clones are obtained that produce antibodies that only react with the antigen when it has been immobilized on the surface of the ELISA plate, but that fail to detect the same antigen in solution. Such antibodies that only bind to immobilized antigen are usually of limited value since they will not work in a lot of assays. Correspondingly some antibodies may only bind when the antigen is in solution and not when immobilized, thus risking missing important reactivities if only testing against coated antigen.

In the present invention, because the antibody binds the antigen in solution, it is more representative and will not only detect antibodies capable of binding immobilized antigen. Measuring antibodies that only bind to the immobilized antigen, and not the soluble antigen, may give a skewed picture and involve a significant risk that the results obtained do not reflect the functional capacity of the antibodies. Therefore, measuring against soluble antigen, as in the new assay, is a further significant advantage with results also more likely to better predict and correlate to the biological activity.

With the conventional method, epitopes may be masked or the antigen denatured on immobilization to the ELISpot plate. In the assay method of the invention a potential interference by the conjugation with a tracing label may occur. However, this can be better controlled with the new method where binding of the label can be achieved under controlled conditions with different types of defined chemistry. Also if one labeling method involves the blocking of a certain epitope and another method a different epitope a mixture of the two differently labeled antigens may ensure availability of both epitopes.

The new ASC assay method allows cells producing antibodies to multiple antigens to be detected and distinguished in the same well of the plates by using differentially labelled antigens for detection. This enables more qualitative data to be provided and also has the advantage that fewer cells are needed to analyze production of antibodies to two or more antigens than when each antigen is analyzed in a separate well. Using the invention it is possible to characterize the number of cells producing antibodies against each of a panel of antigens.

These advantages of the assay of the invention make it particularly useful in diagnostic applications. The assays of the invention can potentially substitute and/or complement many of the existing serological assays used in the diagnosis of, for example, many types of infections, allergies and autoimmune conditions. Given the exquisite sensitivity of the assay of the invention it is likely to be more sensitive than current serological assays and could therefore allow earlier and more reliable diagnosis. In many infections ASCs appear before there are significant levels of antibodies in the serum. Thus, by measuring antibody secreting cells earlier detection can be achieved. That may be a particular advantage for infections, such as HIV, where early detection is an advantage.

Since the assay allows the simultaneous detection of antibodies to more than one antigen, it can also be used to distinguish between, for example, different infections with similar symptoms or different allergies. Thus, the presence of antigen secreting cells against a panel of antigens may be assessed.

The new assay also has significant applications in research (e.g. vaccine research and development). More specifically, the inventors have demonstrated that the assay of the invention may be used to determine antibody specificity. This means that the assay can be used to investigate the immune response generated following infection, immunisation, vaccination or exposure to an allergen. In particular, the assay may be used to identify the part of an antigen or allergen to which the antibodies generated bind and this will, for instance, provide new and valuable information about the quality of the B cell response against a given antigen of interest.

The assay of the invention has been shown to be particularly effective in measuring the presence of ASC against the envelope (Env) glycoprotein, particularly that of HIV-1. Env is found in the viral membrane and is important for mediating viral entry into target cells through binding to host cellular receptors and mediating fusion of the virus membrane and the host cell membrane. HIV-1 Env is composed of a complex of gp120 and gp41 subunits, which bind to CD4 and a co-receptor, usually CCR5 or CXCR4. As shown in the Examples provided here, employing the assay of the invention in measuring ASC that are specific for Env can be used to measure the presence of antibodies against HIV. A similar approach can be taken to measure ASC that are specific for surface proteins of any virus, both enveloped and non-enveloped viruses, as the surface proteins are the main targets for anti-viral antibody responses. Likewise, ASC against bacteria, parasites or other infectious agents can be measured by using different antigen probes and the epitopes being bound by the antibodies produced can be localised and identified.

In a preferred embodiment, where reference is made herein to ASCs, the ASCs are B cells. In one instance, the B cells are memory B cells. However, the invention may be applied to any ASC producing an antibody, hence any cell comprising the genes necessary to produce an antibody.

Accordingly, the present invention provides a method of diagnosing infection, a tumour, autoimmune disease or allergy in a subject by detecting antibody secreting cells specific for an antigen in a sample from the subject, the method comprising:
(a) providing:
(i) a sample comprising antibody secreting cells from a subject;
(ii) a surface on which anti-Ig antibodies are immobilized; and
(iii) a labelled antigen;
(b) contacting the sample and the surface under conditions suitable for antibodies produced by the antibody secreting cells to bind to the immobilised anti-Ig antibodies on the surface;
(c) contacting the surface with the labelled antigen under conditions suitable for the antigen to bind to antibodies specific for the antigen;
(d) detecting any labelled antigen captured on the surface through the presence of a spot or spots, thereby detecting the presence or absence of antibody secreting cells specific for the antigen, wherein the presence of antibody secreting cells diagnoses an infection in the subject.

Such an assay may be performed with a plurality of different antigens, each labelled differently to allow determination of for which of the antigens ASCs producing antibodies specific for the antigen are present. For instance, a panel of antigens may be screened representing antigens from different pathogens or different strains of the same pathogen, to determine which is present. Similarly, a panel of autoantigens or allergens may be screened to determine which is responsible for an allergy or autoimmune disorder.

In another embodiment, the present invention provides a method of monitoring a humoral immune response, the method comprising:
(a) providing:
  (i) a sample comprising antibody secreting cells from a subject;
  (ii) a surface on which anti-Ig antibodies are immobilised; and
  (iii) a plurality of different antigens, each differently labelled;
(b) contacting the sample and the surface under conditions suitable for antibodies produced by the cells to bind to the immobilised anti-Ig antibodies on the surface;
(c) contacting the surface with the labelled antigens under conditions suitable for the antigens to bind to antibodies specific for the antigens;
(d) detecting any labelled antigen captured on the surface for each of the different antigens, thereby determining whether or not antibodies specific for each antigen are present in the sample.

The present invention also provides a method of monitoring a humoral immune response, the method comprising:
(a) providing:
  (i) a sample comprising antibody secreting cells from a subject;
  (ii) a surface on which anti-Ig antibodies are immobilised;
  (iii) a first labelled antigen; and
  (iv) a second labelled antigen;
(b) contacting the sample and the surface under conditions suitable for antibodies produced by the cells to bind to the immobilised anti-Ig antibodies on the surface;
(c) contacting the surface with the first labelled antigen under conditions suitable for the antigen to bind to antibodies specific for the antigen;
(d) contacting the surface with the second labelled antigen under conditions suitable for the antigen to bind to antibodies specific for the antigen;
(e) detecting any first labelled antigen captured on the surface and any second labelled antigen captured on the surface, thereby determining whether or not antibodies specific for the first and/or second antigen are present in the sample.

The present invention further provides a kit for determining the specificity of antibodies generated in response to a pathogenic agent or tumour cell, the kit comprising:
(i) a surface on which anti-Ig antibodies are immobilised;
(ii) a first labelled antigen; and
(iii) a second labelled antigen,
wherein the first and second labelled antigen are different molecules, or fragments of molecules, derived from the same pathogenic agent or tumour cell.

The invention additionally provides a method of detecting an antibody secreting cell specific for an antigen in a sample from a subject, the method comprising:
(a) providing:
  (i) a sample comprising antibody secreting cells from a subject;
  (ii) a surface on which anti-Ig antibodies are immobilized; and
  (iii) a labelled antigen;
(b) contacting the sample and the surface under conditions suitable for antibodies produced by the antibody secreting cells to bind to the immobilised anti-Ig antibodies on the surface;
(c) contacting the surface with the labelled antigen under conditions suitable for the antigen to bind to antibodies specific for the antigen;
(d) detecting any labelled antigen captured on the surface through the presence of a spot or spots, thereby detecting the presence or absence of antibody secreting cells specific for the antigen.

In one preferred embodiment of the invention, the assay or method of the invention is an ELISpot type assay or method. In another, preferred embodiment, the assay or method of the invention is an Fluorospot type assay or method.

The present invention also provides a method of monitoring a humoral immune response, the method comprising:
(a) providing:
  (i) a sample comprising antibody secreting cells from a subject;
  (ii) a surface on which anti-Ig antibodies are immobilised; and
  (iii) a plurality of differently labelled antigens;
(b) contacting the sample and the surface under conditions suitable for antibodies produced by the cells to bind to the immobilised anti-Ig antibodies on the surface;
(c) contacting the surface with the labelled antigens under conditions suitable for the antigens to bind to antibodies specific for the antigens; and
(e) detecting each differently labelled antigen captured on the surface, thereby determining whether or not antibodies specific for each of the plurality of antigens are present in the sample.

BRIEF DESCRIPTION OF THE FIGURES

In FIG. 6a, total IgG-producing cells are measured by coating the wells with a polyclonal anti-mouse IgG antibody. The same antibody conjugated to biotin is then used for detection of spots. In FIG. 6b, Env-specific ASC cells are detected using a conventional ELISpot assay, in which the antigen is coated in the ELISpot plates. In FIG. 6c, the wells are coated in the same way as in FIG. 6b, and biotinylated Env is used to visualize the spots corresponding to Env-specific antigen secreting cells.

DETAILED DESCRIPTION OF THE INVENTION

Figure 1:
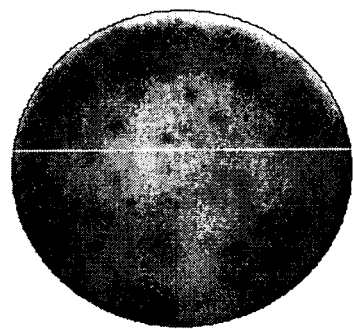
FIG. 1 shows a comparison between the conventional and the alternative assay of the invention using hybridoma cells producing antibodies to human IgE and IL-2.
Figure 1:
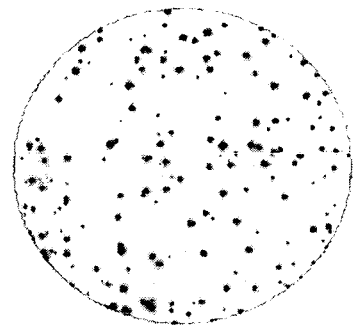
Figure 1:
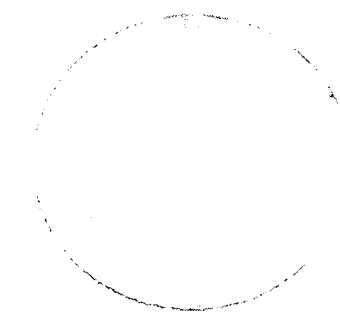
Figure 1:
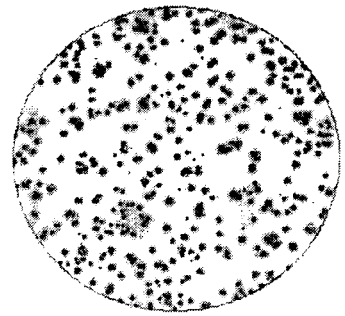

The present invention provides an assay having several surprising advantages over the conventional ELISpot assay that make it particularly useful in diagnostic settings and to investigate antibody responses. The assay typically comprises:
(a) providing:
    (i) a sample comprising antibody-secreting cells;
    (ii) a surface on which anti-Ig antibodies are immobilised; and
    (iii) a labelled antigen;
(b) contacting the sample and the surface under conditions suitable for antibodies secreted by the cells to bind to the immobilised anti-Ig antibodies on the surface;

(c) contacting the surface with the labelled antigen under conditions suitable for the antigen to bind to antibodies specific for the antigen; and (d) detecting any labelled antigen captured on the surface.

The antibodies secreted by the cells are captured on the surface by binding to immobilised anti-Ig antibodies in the vicinity of the antibody-secreting cell. The labelled antigen present on the surface therefore reveals spots on the surface, with each spot representing a cell secreting the antibody that binds to the antigen of interest. In a preferred embodiment of the invention, a key feature is that it is the antigen that is labelled. That means that what is being measured is antibody secreting cells which produce an antibody reactive against the labelled antigen, not the overall number of ASCs, or overall number of ASCs producing a particular antibody isotype.

Cell Sample

Any antibody-secreting cell (ASC) may be used in the assay of the invention. Suitable cells include freshly isolated cells from peripheral blood or from various lymphoid tissues (e.g. mucosa, bone marrow, spleen and/or lymph nodes) and cultured cells (e.g. short term cultures of freshly isolated cells or hybridoma cells). In some instances, samples may comprise, or consist essentially of, B cells. Samples may, in some instances, comprise other cells than B cells (e.g. PBMC also containing T cells, NK-cells and monocytes) or may be purified B cells. B cells may also be of different maturation/differentiation stages including memory B cells and plasma cells. Thus, the sample my comprise memory B cells or consist essentially of such cells. In some instances, the sample may comprise, or consist essentially of, plasma B cells. In further instances, both plasma B cells and memory cells may be present and the sample may comprise or consist essentially of such cells. In one instance, the assays of the invention may be employed to detect and/or measure memory B cells.

In some embodiments, no purification or enrichment of ASCs, particularly B cells, may be performed. In some instances, PBMCs or splenocytes may be employed without further purification or enrichment of the cells.

Cells isolated from a subject may be tested ex vivo or may be cultured in vitro prior to use in the assay. For example, where it is wished to investigate antibody production by memory B cells, memory B cells may be stimulated in culture prior to use in the assay. In some embodiments the cells may be unstimulated.

Any suitable sample containing the cells of interest may be used in the assay. Peripheral blood is the preferred source of cells from a human or primate subject. Cells may also be collected from bone marrow, mucosa, spleen or cerebrospinal fluid.

When the subject is a smaller laboratory animal, such as a mouse, peripheral blood may be used, but due to the limited number of cells that can be obtained from peripheral blood, it is more common to prepare cells from the spleen which is a rich source of B cells.

Generally, the ASCs which are provided for use in a method of the invention are taken from the subject in a blood sample, although other types of samples which contain ASCs can be used. The sample may be added directly to the assay or may be processed first. In some instances the processing may comprise diluting the sample, for example with medium or buffers. The sample may be diluted, for example, from 1.5 to 100-fold, for example 2 to 50 or 5 to 10-fold.

In other instances, the sample may effectively represent a concentration of the cells in comparison to their original density in the sample taken from the subject. For instance, when using PBMC from the blood the population of PBMC in blood is typically around 1 million cells/ml of blood. So when adding a sample of maybe 400,000 PBMC/well in a volume of 100 to 200 microliters, the cells are actually in a higher concentration than they would be found in the blood. Hence in some instances, the cells may effectively be concentrated at least two, five, ten or twenty fold or up to such levels.

Such concentration may be achieved by any suitable means. For instance, PBMC are typically separated from blood by Ficoll separation leaving the PBMC fraction as a band on top of the Ficoll. By collecting this band and spinning the cells down by centrifugation one can then suspend the cells in any volume of medium and often the volume used is smaller than the original volume of blood from which the cells were isolated and hence the effective concentration of the cells. Other purification techniques, such as MACS may also lead to concentration.

In some situations the antibody secreting cells secreting antibodies against the antigen of interest will form only a small proportion of the total cells/the total antibody secreting cells. For instance, the number of cells it is possible to put in a well of a 96-well plate is typically limited to around 400,000 cells for human PBMC. As B cells make up a portion of the cells in PBMC (around 5-10%), only 20,000 to 40,000 B cells will typically be present in each well. Simply increasing cell numbers may lead to the formation of multiple cell layers which is not ideal as secretion from cells that are at some distance from the membrane with the capture antibodies may result in bigger and more diffuse spots. Thus, rather than overload wells with cells, cell purification may be used to help detect the antibody secreting cells, particularly in the case of low responses where the desired antibody secreting cells may only be present in limited numbers.

The processing may comprise separation of components of the blood or other samples. For example, samples of peripheral blood mononuclear cells (PBMCs) or mononuclear cells (MCs) of other origin are prepared. In another embodiment, only ASCs and in particular B cells are purified from the samples. In one instance, antibodies against cell markers are used in the purification, for instance via the use of magnetic bead systems such as MACS. MCs, PBMCs and ASCs, particularly B cells, can be separated from the samples using techniques known in the art, such as those described in Lalvani et al (1997), J. Exp. Med. 186:859-865.

Markers which may be used to achieve purification of ASCs, and in particular of B cells include, for instance, CD19 and CD20, and in particular CD19. CD40 and CD23 are expressed on B cells, but are also found on other cell types, for instance CD40 is expressed in monocytes and dendritic cells. Thus, purification via CD40 and CD23 may be used if it is not necessary to remove the other cell types or alternatively where additional purification steps will be used to remove them.

Antibodies against any of CD19, CD20, CD23 and CD40 may be employed in the purification, preferably against CD19 and CD20 and in particular against CD19. In one instance, it may be desired to purify plasma B cells. At the plasma cell stage, B cells have lost many surface markers, including those mentioned above so, if wishing to isolate these, one needs to use specific plasma cell markers, for instance CD138.

In one embodiment, negative selection may be employed in the cell purification. Negative selection may be used to remove, for instance, T cells, NK cells and monocytes using markers such as CD3, CD14 and CD16. It may be desired to purify all B cells, including plasma cells, and negative selection may be one approach used to do so. Purification of all B cells may also be achieved by positive selection using a marker selected from CD19 and CD20 in combination with a second marker, which is CD138. Any of the positive and negative selection protocols outlined herein may be combined.

In one instance, the ASCs used in the assay are in the form of unprocessed or diluted samples, or are freshly isolated ASCs (such as in the form of freshly isolated MCs or PBMCs) which are used directly ex vivo, i.e. they are not cultured before being used in the method. However, in other instances the cells may have been cultured and/or may have been stimulated. In some embodiments stimulation and cultivation may be performed in separate wells or directly in the assay wells.

Subject

The subject from which the cells are taken may be a human or animal subject. In a preferred instance the subject is human. The animal subject is preferably a mammal, such as a primate or smaller mammal, for example a mouse, rabbit, rat or guinea pig. In one instance, the non-human animal is one that is commonly used for experimental research in a laboratory.

The subject, whether human or animal, may have been immunized or vaccinated against an infectious agent or other antigen. Alternatively, the subject may have been exposed to an infectious agent or may be considered to be at risk of having been exposed to an infectious agent. The subject may be exhibiting symptoms of an infection.

The subject, whether human or animal, may be suffering from an allergy or have been exposed to an allergen.

The subject, whether human or animal, may have an autoimmune disease, or may be exhibiting symptoms of an autoimmune disease.

The subject may have a genetic or acquired disposition to allergy or to an autoimmune disease.

The subject may be a transgenic or knock-out animal, particularly such a rodent and preferably such a mouse or rat. The knock-out animal may lack, or have disrupted, the endogenous gene for the antigen the animal is immunized with.

The invention may be employed in a veterinary setting. Thus, in one instance, the subject may be a non-human animal that is commercially reared or farmed. For instance, the animal may be bovine, ovine or porcine. The animal may be a horse and in particular a racehorse. The animal may be a pet. For instance, it may be a cat or dog.

In cases where the antigen detected is the same for humans as the animal, the antigen employed in the assay may be the same, but with an anti-immunoglobulin antibody employed appropriate for the species. For instance, that may be the case for *Borrelia* and *Ehrlichia*.

The subject may, in one preferred instance, not be an adult subject. For instance, the subject may be a child, infant or baby, particular a human child, infant or baby.

Surface

The anti-Ig antibodies are immobilised on a surface. Any suitable solid surface may be used, for example, it may comprise, or consist essentially of, a polyvinylidene difluoride (PVDF) membrane. Typically, the antibody may be distributed evenly over the area it is present on. The surface may be the base of a well, such as a well of a microtitre plate. The plate may be suitable for automation of the assay. Typically, the microtitre plate is an ELISpot plate. The microtitre plate may, for instance, contain 24, 48 or 96 wells and in particular 96 wells. Where a microtitre plate is used, separate assays can be carried out in separate wells of the plate. Where a specific number of cells is referred to herein in relation to a particular plate size, the number may be modified when a different size plate is used so that an equivalent number of cells is employed.

In some instances, assays may measure the production of antibodies against a plurality of different antigens in the same well. For instance at least two, three, four or five different antigens in the same well.

Conditions suitable for coating the surface with antibodies are well known in the art. Generally, an antibody may be bound to the surface by contacting the surface with the antibody under conditions suitable for antibody binding and washing to remove unbound antibodies. The surface may be "blocked" prior to addition of the cells. Suitable blocking agents are well known in the art and include bovine serum albumin (BSA), casein or fetal calf serum.

The aim of blocking is typically to saturate the binding capacity of the surface in order to minimize binding of the secondary detection reagents and thereby preventing background. However, blocking is an optional step and in some instances, the method may not involve a blocking step. For instance, the cells may be cultured in medium containing large amounts of protein (e.g. fetal calf serum) so that the surface will become effectively blocked during the culturing and hence a separate blocking step would be redundant.

Coating Antibody

The solid surface may be coated with an anti-Ig antibody, or other affinity ligand, which has the capacity to bind to an Ig antibody. The antibody or other affinity ligand may have the capacity to bind to an antibody of a certain species, such as human Ig or mouse Ig. The antibody or other affinity ligand may be specific for a particular antibody isotype, such as IgG, IgA or IgM or to a subclass of a particular isotype, such as IgG1, IgG2, IgG3 or IgG4. The use of antibodies or other affinity ligands specific for a particular isotype or subclass allows qualitative information about the antibodies to be obtained. For instance, from a diagnostic viewpoint as well as in a vaccine setting it may be of interest whether an antibody response is primarily of IgM, IgG, IgA or IgE isotype.

In some instances an antibody fragment may be employed. The fragment must be capable of binding the antibody secreted from the ASCs. In one instance, the fragment may be a $F(ab')_2$, $F(ab)_2$, Fab', Fab or Fv fragment. Reference herein to an antibody encompasses such functional fragments. In one instance, the antibodies are full antibodies and not fragments.

After allowing the antibodies to immobilize on the surface, for example by overnight incubation at +4 to +8° C., excess antibodies are washed away and the surface may optionally be saturated with a blocking reagent such as bovine serum albumin (BSA).

Addition of Cells to Surface

In a method of the invention, the sample of cells is introduced into the well or brought into contact with the surface comprising the immobilized antibodies, or other affinity ligands, under any conditions suitable for antibody production. The conditions are also suitable for the antibodies produced by the cells to bind to the immobilised antibodies, or other affinity ligands.

The number of cells added to each well of the assay plate will depend on the size of the well, the size of the cells and the expected frequency of positive cells. For example when investigating monoclonal hybridoma cells the number of cells added to a typical 96-well ELISpot plate may be up to about 5,000, preferably up to about 3,000 and even more preferably up to about 2,000 cells. For samples with an expected low frequency of antigen-specific cells like PBMC or spleen cells from a naturally infected subject, the number of cells per well of a 96 well plate may, for instance, be up to about 750,0000, preferably up to about 500,000 and even more preferably up to about 400,000 cells. Equivalent cell numbers may be used for different plate sizes.

In one preferred instance, account is taken of the expected or estimated frequency of antibody secreting cells when determining the number of cells to be added per reaction. For instance, some of the experimental work described herein employs cloned hybridoma cells that would all be expected to potentially be able to produce antibody against the antigen of interest and hence give a spot. In such instances, only very low numbers of cells may be needed, for instance 5,000 or less, preferably 2,500 or less, more preferably 2000 or less and in some instances as low as about 100 cells. Hybridoma cells may, in some instances, be employed as controls or as a model system.

For spots to be counted readily in a well in a 96-well plate ideally around 1500 spots should not be exceeded as above that level the spots will start to float into each other which will make counting (both manually and with a reader) harder. Thus, when determining how many cells to use, the expected frequency of positive cells will preferably be taken into account to ensure that level is ideally not exceeded.

In many applications, the expected instance of positive cells will be much lower as cells producing antibodies against the antigen of choice are expected to be in the minority. In a preferred instance, the number of cells employed will be, or be equivalent to, between 25,0000 to 1,000,0000 cells, preferably between 50,000 to 750,000 cells, more preferably between 75,000 to 500,000 and in particular between 100,000 to 400,000 cells. In one instance, such cell numbers may be employed when using PBMC or spleen cells.

When performing the method of the invention on samples from vaccinated subjects with strong immune responses the number of cells employed may, for instance, be less, as may be the case where purified ASCs are being employed, as the proportion of positive cells is expected to be greater. For instance, around a half, a quarter, a fifth, a tenth or less of the above specified cell numbers may be used in some embodiments. In instances where several antigens are being studied in the same well, such lower numbers may also be used to ensure the number of spots per well is readily countable.

Unlike T cells, which may require the presence of antigen presenting cells and cellular contact and consequently a certain cell density to achieve optimal antigen stimulation, the same does not typically apply to antibody secreting cells, such as B cells. Thus, measuring small numbers of cells should still be possible.

In some instances, serial dilutions of the initial sample may be made and different levels of dilution assessed for the number of antibody secreting cells present. Cell numbers may be assessed by any appropriate means.

The cells are left to incubate for sufficient time for antibody production to take place. The assay may be carried out in any suitable volume. Typical volumes of the cell sample range from about 10 µl to about 1 ml, preferably from about 50 µl to about 500 µl, more preferably from about 100 µl to about 200 µl. Typically, the length of time for which the cells are incubated with the solid surface is from about 4 to about 50 hours, for example from about 6 to about 48 hours from about 8 to about 45 hours, from about 12 to about 36 hours or from about 16 to about 32 hours, preferably from about 6 to about 16 hours, for example overnight. In some instances, the incubation may be longer, for instance, for up to a week, up to five days, four days, three days or two days.

In one instance, overnight incubation is employed where no separate activation of the cells is performed once the cells have been obtained from the subject.

In one embodiment of the invention, the cells may be stimulated and cultured at the same time. Thus, both may be performed simultaneously in the assay vessel. Thus, for instance, such an approach may be employed when detecting the presence or absence of memory ASCs (particularly memory B cells).

In such instances, it may be that the cultivation and stimulation stage is, for instance, up to ten days, up to a week, up to four days, up to three days, up to two days or one day or less in length. In a preferred instance, the step is about 2 to 3 days in length.

In some instances the ASCs being measured are not B cells. For instance, it is possible to produce experimentally cells that produce antibodies that are not B cells (e.g. through transfection of Ig genes into other cells or antibody fragments produced by phage display). Hence the invention may be employed to identify any Antibody Secreting Cells, such as any cell comprising and expressing the necessary genes to produce a functional antibody. Hence, in one instance the invention may be applied to detect any ASCs that have assembled immunoglobulin genes to allow for the expression of an immunoglobulin.

The cells may be incubated at any suitable temperature. The suitable temperature is typically in the same range as the normal body temperature of the human or animal from which the cells are derived. Typically, the incubation is carried out at a temperature between about 35° C. and about 39° C., preferably from about 36° C. to about 38° C., more preferably at 37° C.

In a preferred instance, the cells may be incubated in cell culture medium, ideally with necessary growth supplements such as serum (e.g. fetal calf serum) and, in some cases, cytokines (e.g. BAFF, IL-6, IL-10 and/or IL-21). General conditions known to apply to particular cell types may be utilised.

In some instances, it may be desired to activate the antibody secreting cells. For instance, when testing memory responses, stimulation of the cells may be performed. This may be done by, for instance, adding polyclonal stimulators like PWM (pokeweed mitogen) or one or more defined signals like CpG, CD40 ligand or ASC, particularly B cell, stimulatory cytokines (e.g. BAFF, IL-6, IL-10, IL-21). Preferably, the stimulus will stimulate as many ASCs, typically B cells, as possible into antibody production in order to be able to detect those which secrete antibodies to the antigen that is tested for. Alternatively, in some instances, cells may be stimulated by incubating them with the specific antigen together with costimulatory signals (for instance stimulation through CD40) that more specifically stimulates the antigen-specific antibody secreting cells.

In many cases cells may not be stimulated after isolation. For instance, if looking at circulating antibody secreting cells, in particular plasma cells, that already secrete antibodies, as could be the case if taking a sample from a recently vaccinated subject or someone with acute infection, the addition of a stimulator after isolation may, for instance, not be employed, as the cells may well have already been stimulated in vivo.

Non-stimulated cells, such as PBMC or spleen cells, may be used to investigate the effect of a vaccination/immunization or to differentiate between an acute or old/latent infection. Stimulation may be used when assaying for memory cells, particularly memory B cells, thus PBMC or spleen cells may be used after polyclonal activation (for instance with PWM) to test for presence of memory B cells. The latter can, for instance, be used as a means to look whether an individual has been exposed to an infectious agent as they have memory ASCs against the antigen or whether the subject has unusually many cells with capacity to produce autoantibodies. Such an approach may be employed when assessing allergies and autoimmune disorders. It may also be used in a vaccination setting to look for and monitor the long-lasting effect of a vaccine and determine whether memory ASCs are generated.

The antibodies produced by the antibody secreting cells will bind to the capture antibodies at the site of the producing cells. Antibodies from all secreting cells will be bound independent of antigen specificity.

Prior to detection of bound antibodies of interest the cells are removed, typically by washing. Suitable washing conditions are well known in the art.

Label on Antigen/Detection Methods

To detect the bound antibodies of interest a labelled antigen is added to the surface. Where it is wished to detect antibodies to more than one antigen a mixture of several antigens may be used. Suitable labels are well known in the art. The antigen(s) may be labelled with, for example biotin, an enzyme or a fluorochrome. The different antigens may be labelled in the same way or differently.

For example, where the antigens are from the same allergen or infectious agent and it is wished to diagnose an allergy or infection the antigens may each be labelled in the same way. Conversely, when it is wished to distinguish between antibodies having different specificities the different antigens are labelled differently so that reactivity against separate antigens may be analysed in the same well. The different labels may be different fluorochromes or different enzymes. If biotin is used an additional detection reagent, such as streptavidin conjugated with enzyme or a fluorochrome, is required. When using enzyme, a precipitating substrate is added after the antigen-enzyme conjugate has bound and a coloured spot will appear at the site of the producing cell. The number of spots can then be counted in an ELISpot reader. If fluorochromes are used, it may be that no additional step is required as the spots can be examined directly in an U.V. microscope or a fluorospot reader.

Reference to labelled antigen includes indirect labelling where the antigen is bound by another entity that includes the actual measured label, such as the antigen being biotinylated and then streptavidin conjugated to a label is employed to visualize the antigen.

In one preferred embodiment, the antigen or antigens are labelled fluorescently. In a particularly preferred embodiment, the detection is performed by means of fluorospot analysis. The use of different coloured antigens, particular fluorescent antigens, can allow the presence of antibody secreting cells producing antibodies against a plurality of antigens to be measured simultaneously. For instance, to measure the presence or absence of a plurality of different antigens from the same pathogen, a plurality of the same antigen from different pathogens, a plurality of different antigens from different pathogens and/or a plurality of variant forms of antigens distinctive to variants of the same pathogen. For instance, the invention may be employed to detect the presence of antibody secreting cells against a panel of different influenza strains.

Thus, in one instance, the assay may be used to screen a panel of such antigens to detect which of the panel there is an immune response against. For instance, the panel may be used to identify which of a panel of influenza viruses there is an immune response against. Similarly, by testing for immune responses against a number of antigens, the invention may be employed to check if all of the desired components of a vaccine elicit an immune response, such as the HA and NA components of an influenza virus or that vaccines against several pathogens result in an immune response against each pathogen. A panel of autoantigens or a panel of allergens may also be similarly screened to identify those ASCs against are present. Hence, the invention may be used, in one instance, for allergy testing.

In some instances, the response being measured may be the existence of memory B cells.

Fluorochromic labelled antigens may be used for detection. The use of different fluorochromes is preferred when it is wished to simultaneously detect and enumerate antibody-secreting cells to several different antigens in the same well in, for instance, a diagnostic setting. This enables more than one type of infection in a single well to be analyzed or the presence of antibodies to more than one allergen or auto-immune target antigen to be demonstrated.

Generally, the antigen is labelled with a label that may be detected either directly or indirectly. A directly detectable label may comprise a fluorescent label such as fluoroscein (particularly Oregon green) and rhodamine (particularly Texas red).

In one particularly preferred embodiment of the invention where it is desired to detect or measure ASCs producing antibodies against a plurality of antigens, fluorescence may be employed. Fluorescence is a preferred method whenever investigating ASCs to a plurality of antigens and where one wishes to discriminate the reactivity to the different antigens.

As described above it is easiest to envisage the situation where each antigen is labelled with a different fluorochrome. This is the ideal and preferred situation as this makes the assay extremely simple since, after the incubation with the cells, there is typically only one incubation (i.e. with the different labelled antigens) before the results can be evaluated. Thus, the use of differently coloured fluorochromes allows simultaneous detection of ASCs producing antibodies against a plurality of antigens.

In some instances, an enhancing step may be employed in the assays of the invention to increase sensitivity of detection, particularly where fluorescence is being employed. This means that one has to put a "tag" on the antigen (e.g. biotin) that can then, in the particular case of biotin, be combined with Streptavidin or avidin that has been labelled with a fluorochrome. Hence such indirect detection may be employed.

Apart from biotin—Streptavidin, biotin-Fitc (fluorescein isothiocyanate) may, for instance, be employed, which in itself is fluorescent but can also be combined fluorescent labelled anti-Fitc antibodies.

The binding of a fluorescently labelled antigen to the immobilised binding antibody complex may be detected in a fluorescent microscope or in a fluorospot reader.

A label that may be detected indirectly may comprise an enzyme which acts on a precipitating non-fluorescent substrate that can be detected under a conventional low-magnifying, for example 10 times magnification, 20 times magnification or 50 times magnification, microscope such as a stereomicroscope or using an automated ELISpot reader. A magnifying glass may alternatively be used to distinguish the spots. An automated ELISpot reader is typically based on a video camera and image analysis software adapted for the analysis of spots. Preferred enzymes include alkaline phosphatase and horseradish peroxidase.

Other indirect methods may be used to enhance the signal. For example, the antigen may be biotinylated allowing detection using streptavidin conjugated to an enzyme such as alkaline phosphatase or horseradish peroxidase or streptavidin conjugated to a fluorescent probe such as fluoroscein (particularly Oregon green) and rhodamine (particularly Texas red).

In all detection steps, it is desirable to include an agent to minimise non-specific binding of the antigen. For example bovine serum albumin (BSA) or foetal calf serum (FCS) may be used to block non-specific binding.

In some instance, the total number of antibody secreting cells present in a sample may be determined by carrying out a positive control assay in which the labelled antigen used for detection is replaced with a labelled anti-Ig antibody. This enables the proportion of cells in a sample secreting an antibody of interest to be determined.

Reference anywhere herein to a plurality may, in a preferred instance, refer to at least two, three, four, five, six, or seven different entities or in other preferred instances up to, or including, ten, eight, six or four. Instances of preferred ranges include from two to ten, eight, six or four, from four to ten, eight or six or any combinations thereof.

Analysing Data

A total IgG assay may be carried out in parallel to an assay of the invention or as part of such an assay. This will allow the proportion of antibody-secreting cells secreting antibody of interest to be determined. In some instances, a negative control may be performed using a surface lacking anti-Ig antibodies. In a preferred instance, such a negative control may be unnecessary.

In one embodiment, a sample from a subject known to produce antibodies against a particular antigen may be used as a positive control. Alternatively, hybridoma cells producing the relevant antibody may be used as a positive control. In other instances a sample from a subject lacking reaction may be used as a negative control or a sample from a subject known not to have been exposed to the antigen may be used as a negative control.

The numbers of cells secreting different antibodies of interest may also be enumerated in an assay of the invention and compared. The number of cells secreting antibody per unit volume of the sample may be calculated. In some assays this may be done for several antigens.

The number of antibody secreting cells may be measured over several time points and in some instances plotted over time to show the development of an immune response over time.

In some instances, the size and/or intensity of the spots produced may be studied. This may be used as a guide to how much antibody the antibody secreting cells are producing. For instance, the diameter of spots may be measured, the average diameter of spots may be measured and/or the number of spots below or over a given diameter may be measured. In some instances, the area of the spots may be measured and/or the number of spots under or above a certain area. Such measurements may be used as a way of determining if a given stimulus results in higher levels of antibody production compared to an untreated control. It may be employed as a measure of the activation of antibody secreting cells.

The assays of the present invention typically allow detection at the single cell level. They typically measure localised antibody production by cells. In that respect immobilisation of an anti Ig antibody is shown by the present application to give unexpectedly superior results to immobilisation of antigen. Some prior art ELISA based methods refer to immobilising anti Ig antibodies. However, in the case of an ELISA such an approach was not commonly employed because antigen specific antibodies would have to compete for binding with the antibody content of the sample as a whole giving a weak signal. The present invention therefore goes against the mindset of immobilising antigen.

Diagnostic Applications

The present invention provides a method of diagnosing an infection, tumour, autoimmune disease or allergy in a subject by detecting antibody secreting cells specific for an antigen in a sample from the subject, the method comprising:
(a) providing:
  (i) a sample comprising antibody secreting cells from a subject;
  (ii) a surface on which anti-Ig antibodies are immobilized; and
  (iii) a labelled antigen;
(b) contacting the sample and the surface under conditions suitable for antibodies produced by the antibody secreting cells to bind to the immobilised anti-Ig antibodies on the surface;
(c) contacting the surface with the labelled antigen under conditions suitable for the antigen to bind to antibodies specific for the antigen;
(d) detecting any labelled antigen captured on the surface, thereby detecting the presence or absence of antibody secreting cells specific for the antigen, wherein the presence of antibody secreting cells diagnoses an infection, allergy, tumor or autoimmune condition in the subject.

In a preferred instance, the number of spots produced is measured.

As discussed above, multiple different antigens may be tested, including a plurality of different antigens, each differently labelled, preferably with the determination being done simultaneously for all of the antigens.

Preferably, in a diagnostic setting the antibody-secreting cells are obtained, for example, from a sample of PBMCs. Generally, no in vitro proliferation step is required.

The invention may be applied for diagnosis involving any of the various antigens associated with the infections, autoimmune conditions, tumours and allergies mentioned herein.

In one instance the invention is used to detect the presence or absence of an immune response against a tumour and in particular such an immune response elicited by therapy.

In one instance, what is detected is an immune response against a therapeutic agent being administered to a subject. Such immune responses may reduce the efficacy of a therapy and hence their detection/monitoring is important. For instance, antibody secreting cells producing antibodies against a therapeutic agent, for example against a viral vector, liposome, therapeutic antibody, drug or transplanted material, may be measured.

Infectious Agents and their Antigens

The method of the invention may be used to investigate antibody responses to a large variety of antigens.

The method is not restricted to detection of human antibodies but can be applied to animals, in particular in veterinary medicine both as a diagnostic method and as an investigative tool in various immunological studies including vaccine development. In cases where the infectious agent is the same as for human (e.g. the above mentioned infections with *Borrelia* and *Ehrlichia*), the antigens used for detection may be the same while the capture anti-Ig antibodies have to be adapted to the specific species.

Several antigens may be useful for detecting antibodies to a particular infectious agent. Examples include the HIV envelope protein and other HIV proteins such as p24 and p55 from "gag" and p68 and p34 from the "pol" gene. *Borrelia* antigens of interest include the flagellin protein, the Osp (outer surface proteins) proteins OspA, OspB, OspC and the C-6 *Borrelia* burgdorfei protein. A mixture of known antigenic agents may be used. Influenza Virus may be diagnosed using hemagglutinins.

In one instance, a panel of influenza antigens may be used to determine which particular antigen is capable of eliciting an immune response, particularly a protective immune response. A panel of subregions or deletion derivatives of influenza antigens may be employed to help localise which particular region is most immunogenic and/or to map epitopes. Such a panel approach may be employed for any of the antigens discussed herein, particularly with fluorescent detection, preferably with a plurality of different coloured fluorochromes to allow immune response against a plurality of different antigens to be measured.

Principally, most types of infections can be diagnosed through the detection of specific antibodies and hence via the detection of ASCs secreting such antibodies. Some examples of infections that may be diagnosed using a method of the invention include in a particularly preferred instance infection with *Mycobacterium tuberculosis* and tick-borne infections like *Borrelia* and *Ehrlichia*. In one preferred embodiment, the assay of the invention is employed to diagnose an acute infection, particularly an acute infection with a tick-borne infectious agent. In a particularly preferred instance, the detection is via fluorescence. The fact immune responses against a plurality of antigens can be readily screened, particularly by using different fluorochromes, means that a plurality of pathogens can be screened for simultaneously to determine which is the infectious agent. Hence, the invention can provide means for rapid and efficient diagnosis of one or more infections. Panels consisting of a plurality of any of the antigens herein may be employed.

In one instance, the antibody secreting cell to be detected may be one producing an antibody against a virus including Human Papilloma Viruses (HPV), HIV, HSV2/HSV1, influenza virus (types A, B and C), Polio virus, RSV virus, Rhinoviruses, Rotaviruses, Hepatitis A virus, Norwalk Virus Group, Enteroviruses, Astroviruses, Measles virus, Para Influenza virus, Mumps virus, Varicella-Zoster virus, Cytomegalovirus, Epstein-Barr virus, Adenoviruses, Rubella virus, Human T-cell Lymphoma type I virus (HTLV-I), Hepatitis B virus (HBV), Hepatitis C virus (HCV), Hepatitis D virus, Pox virus, Marburg and Ebola; bacteria including *M. tuberculosis, Chlamydia, N. gonorrhoeae, Shigella, Salmonella, Vibrio Cholera, Treponema pallidua, Pseudomonas, Bordetella pertussis, Brucella, Franciscella tulorensis, Helicobacter pylori, Leptospria interrogaus, Legionella pnumophila, Yersinia pestis, Streptococcus* (types A and B), *Pneumococcus, Meningococcus, Hemophilus influenza* (type b), *Toxoplama gondii, Campylobacter, Moraxella catarrhalis, Klebsiella granulomatis,* and *Actinomyces israelii;* fungal pathogens including *Candida* and *Aspergillus;* parasitic pathogens including *Taenia,* Flukes, Roundworms, *Entamoeba histolytica, Giardia, Cryptosporidium, Schistosoma, Pneumocystis carinii, Trichomona* or *Trichinella*. The invention may also be used to detect ASCs producing antibodies against Malaria and *Leishmania* antigens.

The invention may be used to detect antibodies against numerous veterinary diseases, such as Foot and Mouth diseases, Coronavirus, *Pasteurella multocida, Helicobacter, Strongylus vulgaris, Actinobacillus pleuropneumonia,* Bovine viral diarrhea virus (BVDV), *Klebsiella pneumoniae, E. coli, Bordetella pertussis, Bordetella parapertussis* and *Bordetella brochiseptica.*

In one instance antibodies may be detected against a member of the *adenoviridae* (including for instance a human adenovirus), *herpesviridae* (including for instance HSV-1, HSV-2, EBV, CMV and VZV), *papovaviridae* (including for instance HPV), *poxyiridae* (including for instance smallpox and vaccinia), *parvoviridae* (including for instance parvovirus B19), *reoviridae* (including for instance a rotavirus), *coronaviridae* (including for instance SARS), *flaviviridae* (including for instance yellow fever, West Nile virus, dengue, hepatitis C and tick-borne encephalitis), *picornaviridae* (including polio, rhinovirus, and hepatitis A), *togaviridae* (including for instance rubella virus), *filoviridae* (including for instance Marburg and Ebola), *paramyxoviridae* (including for instance a parainfluenza virus, respiratory syncitial virus, mumps and measles), *rhabdoviridae* (including for instance rabies virus), *bunyaviridae* (including for instance Hantaan virus), *orthomyxoviridae* (including for instance influenza A, B and C viruses), *retroviridae* (including for instance HIV and HTLV) and *hepadnaviridae* (including for instance hepatitis B).

Antibodies may also be detected against a Reovirus (such as African Horse sickness or Bluetongue virus) and Herpes viruses (including equine herpes). The antigen may be one from Foot and Mouth Disease virus. In a further preferred instance the antigen may be from a Tick borne encephalitis virus, dengue virus, SARS, West Nile virus and Hantaan virus.

In another preferred case the antibody may be from a *retroviradae* (e.g. HTLV-I; HTLV-11; or HIV-1 (also known as HTLV-111, LAV, ARV, hTLR, etc.)). In particular from HIV and in particular the isolates HIVI11b, HIVSF2, HTV-LAV, HIVLAI, HIVMN; HIV-1CM235, HIV-1; or HIV-2. In a particularly preferred embodiment, the antibody may be against a human immunodeficiency virus (HIV) antigen. Examples of preferred HIV antigens include, for example, gp120, gp 160 gp41, gag antigens such as p24gag and p55gag, as well as proteins derived from the pol, env, tat, vif, rev, nef, vpr, or vpu regions of HIV. In a particularly preferred case the antigen may be HIV gp120 or a portion of HIV gp120. The antigen may be from an immunodeficiency virus, and may, for example, be from SIV or a feline immunodeficiency virus.

The invention may be used to detect antibodies against an influenza virus. The influenza antigen may be an influenza NP (nucleoprotein/nucleocapsid protein), HA (hemagglutinin), NA (neuraminidase), M1, M2, PB1, PB2, PA, NS1 and/or NS2 antigens. The influenza virus detected may be from an influenza A, B or C virus, in particular from an influenza A or B virus. The influenza virus may be $H_5N_1$ strain. In one preferred instance, the antigen which is detected is not a hepatitis antigen and in particular not a hepatitis B antigen. In other instances, the antigen is a hepatitis antigen and is a hepatitis B antigen.

The invention may be employed to monitor immune responses against several viral antigens at the same time. For instance, it may be used to measure immune responses against at least two antigens from the same virus, including any of those mentioned herein. In one preferred embodiment, the invention may be used to measure immune responses against at least two different influenza antigens, preferably against hemagglutinin (HA) and neuramidase (NA). In a particularly preferred embodiment, such assays may employ fluorescence to detect the response.

The invention may be used to measure immune responses against antigens from a plurality of pathogens at the same time. For instance, some vaccines are designed to immunize against a plurality of pathogens. The invention may be used to simultaneously measure immune responses against one or more antigens from each pathogen in order to measure the efficacy of a vaccine. In one embodiment, the presence or absence of immune responses against at least two of pertussis, diphtheria and tetanus are measured and preferably against all three simultaneously, preferably to assess the immune response elicited by a vaccine against all three.

In another instance, the invention may be used to determine whether a vaccine against a plurality of strains elicits an immune response against each. For instance, where a vaccine is designed to elicit an immune response against a plurality of influenza strains, labelled antigens specific to each may be used to measure the ability of the vaccine to elicit an immune response against each strain of the virus. Such an approach may be used for any vaccine intended to immunize against a plurality of pathogen strains.

Where the invention is being used to measure immune responses against a plurality of antigens, in a preferred instance different colour fluorophores may be employed for each antigen to allow for simple measure of the results.

The ability to measure immune responses against a plurality of antigens can particularly be an advantage where samples from a subject are only available in small amounts or repeated samples cannot be readily obtained. For instance, in the situation where the subject is a child, in particular an infant and especially a baby.

Allergens, Autoimmune Diseases and Cancer Antigens

The invention also provides methods of investigating antibody responses to allergens, autoantigen and tumour antigens. The assay of the invention may hereby be useful in diagnosing and/or monitoring conditions such as allergy, autoimmunity and cancer.

Allergen-specific responses of different isotypes, such as IgE, IgA and IgG, may be used to diagnose an allergy and to monitor effects of allergen-specific immunotherapy.

In one preferred embodiment ASCs producing IgE will be detected as this isotype that is usually responsible for the allergic symptoms by interacting with and triggering mast cells.

In addition, in many allergies the presence of IgG and/or IgA may have a beneficial effect, for instance as they can potentially neutralize the allergen and minimize its binding to any existing IgE antibodies thereby preventing the triggering of mast cells. Some immunotherapeutic approaches may therefore aim to switch the response from an IgE to an IgG/IgA response. The assay of the invention may be used as a monitoring tool to monitor the switch. Thus, the invention may be used to measure ASCs producing IgE, IgA and/or IgG, and preferably IgE and at least one of IgG and IgA and more preferably all three isotypes and hence may be used to monitor switching between isotypes and hence, for instance, the success of the switching attempt.

Any allergic, or potentially allergic substance, may be used to diagnose allergy to that substance. As an example, major allergens from, for example, birch, cat, dog and house dust mite may be used.

For example, the invention may be employed to detect an immune response, and/or the presence of antibody secreting cells, against an allergen such as, for instance, one from *Ambrosia artemisiifolia, Ambrosia trifida, Artemisia vulgaris, Helianthus annuus, Mercurialis annua, Chenopodium album, Salsola kali, Parietaria judaica, Parietaria officinalis, Cynodon dactylon, Dactylis glomerata, Festuca pratensis, Holcus lanatus, Lolium perenne, Phalaris aquatica, Phleum pratense, Poa pratensis* or *Sorghum halepense*. The allergen antigen may be from a tree, such as, for example, from *Phoenix dactylifera, Betula verrucosa, Carpinus betulus, Castanea sativa, Corylus avellana, Quercus alba, Fraxinus excelsior, Ligustrum vulgare, Olea europea, Syringa vulgaris, Plantago lanceolata, Cryptomeria japonica, Cupressus arizonica, Juniperus oxycedrus, Juniperus virginiana*, or *Juniperus sabinoides*. In some cases the antigen may be from an antigen from a mite such as, for example, from *Acarus siro, Blomia tropicalis, Dermatophagoides farinae, Dermatophagoides microceras, Dermatophagoides pteronyssinus, Euroglyphus maynei, Glycyphagus domesticus, Lepidoglyphus destructor* or *Tyrophagus putrescentiae.*

In some cases antibodies against a tumor antigen (i.e. an antigen that is selectively or more highly expressed in a tumor than in the corresponding normal tissue or may represent an altered (mutated) form of a normal protein) may be detected. Examples of particular cancers where tumor antigens have been identified include cancers of the lung, prostate, breast, colon, ovary, melanoma, a lymphoma and leukaemia. Examples of particular tumour antigens include MART-1, Melan-A, tyrosinase, p97, beta-HCG, GaINAc, MAGE-1, MAGE-2, MAGE-4, MAGE-12, MUC1, MUC2, MUC3, MUC4, MUC18, CEA, DDC, P1A, EpCam, melanoma antigen gp75, Hker 8, high molecular weight melanoma antigen, K19, Tyr1, Tyr2, members of the pMel 17 gene family, c-Met, PSA (prostate antigen), PSM (prostate mucin antigen), PSMA (prostate specific membrane antigen), prostate secretary protein, alpha-fetoprotein, CA125, CA19.9, TAG-72, BRCA-1 and BRCA-2 antigens.

In a particularly preferred instance, the tumour or cancer antigen may be one that the subject has been vaccinated with in order to try and elicit an immune response and the invention may be used to determine whether an immune response has been successfully elicited.

In other instances, the invention may be used to detect antibody-secreting cells against an autoantigen. In particular, the antigen may be an antigen associated with an autoimmune disease. Autoantigens include those associated with autoimmune diseases such as multiple sclerosis, insulin-dependent type 1 diabetes mellitus, systemic lupus erythematosus (SLE) and rheumatoid arthritis. The antigen may be one associated with, Sjorgrens syndrome, myotis, scleroderma or Raynaud's syndrome. Further examples of autoimmune disorders that the antigen may be associated with include ulcerative colitis, Crohns' disease, inflammatory bowel disorder, autoimmune liver disease, or autoimmune thyroiditis. Examples of specific autoantigens include insulin, glutamate decarboxylase 65 (GAD65), heat shock protein 60 (HSP60), myelin basic protein (MBP), myelin oligodendrocyte protein (MOG), proteolipid protein (PLP), and collagen type II.

In one preferred instance, the autoimmune disorder is an autoimmune neurological disorder (myelin) or diabetes (glutamic acid decarboxylase (GAD)).

Any of the antigens discussed herein may be produced by any suitable means. For example, it may be a recombinantly produced protein or manufactured peptide.

A primary goal of prophylactic vaccination is to induce memory ASC responses and/or long-lived plasma cells. The present invention provides improved ASC detection and measurement protocols for the analysis of antibody-secreting cells in vaccinated or infected subjects. By measuring antibody responses at the cellular level rather than at the serological level, frequencies of antigen-specific ASCs, in particular B cells, in different anatomical compartments can be determined.

Infection State

The method of the invention may be useful for discriminating between acute infection and an old or latent infection. In such infections, it is very difficult to tell whether a positive serum test really represents an ongoing infection or just antibodies that remain from a previous infection. Even if antibody titers tend to go down with time, sufficient amounts of antibodies to give a positive reaction may be found years after that the infection has been eradicated.

However, this is not the case if instead the measurement is done at the cellular level, as ASCs with an ongoing production of specific antibodies, have been shown to be present in peripheral blood almost exclusively during the acute infection. This has been established by taking blood cells and cultivating these in absence of any stimulus (i.e. without stimulation of possible memory cells) and after appropriate time (3-4 days) take the supernatants from these cultures and test them in a specific ELISA. This way it has been possible to discriminate between acute infection and old or latent infection.

The assay of the invention provides a more powerful and rapid way of demonstrating this than can be achieved by ELISA. Infections where acute and old or latent infections may be distinguished include in one preferred instance *Borrelia*, *Ehrlichia* and TB.

Thus, in a particularly preferred embodiment, the method of the invention is for determining whether an infection is an acute infection or an old or latent infection, particularly by detecting the presence of peripheral antibody secreting cells producing antibodies against an antigen of the infectious agent. In particular, peripheral ASCs, particularly B cells, may be detected and preferably the relative level of such cells determined.

In some instances, control samples with known numbers of antibody secreting cells representative of an acute and/or old or latent infection may be employed. Measurements may be taken, in some instances, over several time points and/or compared to representative curves or levels expected for acute, old or latent infections.

The number of secreting cells during active disease should, in theory, be similar to any specific response which typically means a low but significant number of spots. Although the level of response is likely to vary significantly between different subjects, as well as between different infections, and will depend on how many antigens that are used for the detection, the number in a subject with an old infection where the infectious agent has been eradicated or in the case of a latent infection, will be extremely low or non-existing in comparison due to a lack of antigenic stimulation. Thus, it should be possible to readily distinguish between an active infection and a latent or old infection employing the invention.

Antibody-secreting cells which spontaneously secrete specific antibodies (i.e. without any in vitro stimulation) are detected in peripheral blood during a very limited time span and will usually disappear within a few weeks after the last immunization. However, antigen-specific antibody secreting cells remain in circulation in the form of long-lived memory cells which after reactivation (polyclonal or antigen-specific) may again become antibody secreting. Thus, very few if any spontaneously secreting cells should be present in peripheral blood in the absence of infection.

Thus, the method may involve comparing the number of antibody secreting cells present with and without stimulation with active infection expected to show much higher numbers of antibody secreting cells without secretion in comparison to latent or previous infection. However, following stimulation those exposed to the infectious agent are expected to display a high number of antibody secreting cells in comparison to those subjects which have never been exposed to the infectious agent.

Multiple Antigens

The assay of the invention may be used to diagnose an infection by simultaneously using antigens to several different pathogens that could potentially be causing the infection. The invention may be employed to determine whether or not antibody-secreting cells producing antibodies against which of a plurality of different antigens are present.

For example, *Borrelia* and *Ehrlichia* bacteria both give similar and very general and often diffuse symptoms (headache, fatigue, fever, muscle ache) that in some cases may go unnoticed. To distinguish the two infections from other infections as well as from each other a patient sample may be tested using one or more labeled antigens from each bacterium. To allow the simultaneous testing of the two infections in the same well and with the same cell sample the two antigens should be differentially labeled with, for instance two different fluorochromes. This approach can be applied to many situations where a differential diagnosis is required and as antigen can be labeled with a variety of fluorochromes a number of potential infections can be investigated simultaneously. Similarly, the approach with differently labeled antigens can be used to investigate antibodies to different autoimmune targets in autoimmune diseases and to different allergens.

The use of a plurality of different antigens may be used to identify which strain of a pathogen is present in a sample particularly which strain of a virus. For instance the antigens employed may be epitopes specific for different strains and with, for instance, each linked to a different fluorochrome. Thus, the invention may be used to identify the presence of particular strains of a pathogen associated with pathogenicity or particularly severe conditions.

A panel of antigens may be assessed using different fluorochromes, for instance two, three, four, five, six or more different antigens or at least such numbers of different antigens.

Vaccine Applications

Vaccination is the prime strategy to combat viral infections in humans. Almost all existing human vaccines, including live attenuated vaccines (such as mumps, rubella, measles and polio "Sabin"), whole-inactivated virus (such as polio: "Salk"), "split-virus" (detergent-disrupted virus preparations such as influenza) and viral subunits (such as hepatitis B and human papilloma particles), are thought to provide protection against infection through their ability to stimulate polyclonal neutralizing antibodies. The method of the present invention may be used to develop new and/or improved vaccines against many globally persistent human pathogens and to test recombinant DNA technology and molecular adjuvants in the development of safe and well-defined vaccine components.

The method of the invention may be used to check that a given vaccine is capable of eliciting, or has already elicited, a humoral immune response against a given antigen. This may extend to whether or not the subject will possess memory ASCs capable of producing antibodies against the variants of a given antigen. This may be employed to check that a particular vaccine can still provide an immune response against variants of a virus and/or that already vaccinated individuals will display a protective immune response when they encounter the new strain. It may also be used to find epitopes for which pre-existing vaccines do not elicit an immune response against in order to identify new epitopes for incorporation in a vaccine.

For instance, the annual inactivated influenza virus vaccine elicits type-specific neutralizing antibodies in vaccinated individuals. This vaccine is highly protective and substantially limits the morbidity and mortality of the seasonal influenza virus epidemics. However, the influenza virus mutates so that a vaccine effective one year is no longer effective the following year. Accordingly, the method of the invention can be used to look for the frequency of memory ASCs that display cross-reactivity with the new hemagglutinin variants of which a new vaccine is comprised. Thus in one instance the invention may be used to identify whether or not memory ASCs will be present which can give rise to a protective immune response against the new strain.

The subunit vaccine employed against the chronic hepatitis B virus is highly protective, but vaccines against other persistent viruses that establish and maintain a chronic infection are less successful and the invention may be employed to help address the problem. For the chronic, highly variable HIV-1, the ability to stimulate broadly neutralizing antibodies through vaccination, as a subset of the polyclonal antibody response, is a long-desired goal. Current models predict that if vaccine-induced immune responses to HIV-1 could substantially lower the level of acute viremia and/or lower the chronic viral load "set-point" within the individual, the transmission rate within the human population would be greatly reduced. Thus, the invention may be employed to determine if immunisation with a particular antigen or vaccine will provide an immune response against a plurality of strains of a pathogen, particular of viral bacterial strains, particularly viral strains and especially HIV strains. The invention may therefore help produce more effective vaccines, particularly vaccines that are effective against a plurality of strains.

The methods of the present invention allow comprehensive analyses (quantitative and qualitative) of infection and vaccine-induced ASC responses as well as ASC responses in allergies, autoimmune diseases and tumorigenic diseases. The ability to characterize ASC responses in greater detail will accelerate the development of successful human vaccines and increase our understanding of anti-viral antibody responses. The Examples provided here describe methods for analyzing HIV Env specific ASC responses, particularly B cell response, but these methods are also widely applicable to other vaccine antigens including any of those mentioned herein.

The present invention provides methods for analyzing the polyclonal ASC responses elicited during vaccination or infection. These methods will enable a better understanding of how broadly reactive ASC responses can be elicited.

The present invention provides new methods for analyzing ASC responses in vaccinated and infected subjects that extend and complement existing analysis of antibody responses. The invention uses a protocol for measuring antigen-specific ASC responses that is more sensitive, has less background and uses less antigen than previously described Elispot assays. The protocol for measuring antigen-specific ASC responses allows the detection and quantification of ASCs producing antibodies of different specificities, exemplified here by using soluble versions of the HIV-1 surface antigen.

For instance, in a vaccine setting as well as from a diagnostic viewpoint, it may be of interest whether an antibody response is primarily of IgM, IgG, IgA or IgE isotype and the invention may be employed to measure in qualitative, or quantitative, terms, cells producing each type of antibody. The invention may be used to monitor over time when the different types of antibodies are produced.

In one particularly preferred embodiment, the invention provides a HIV-related ASC assay using an Env protein that has been prepared and biotinylated in a way that maximally retains the antigenic epitopes as an antigen. The invention also provides a specific ASC cell assay kit which includes biotinylated Env protein. This kit is useful in the evaluation of antibody responses to this protein in vaccine studies (both in humans and experimental animals) and also during natural infection.

Thus, the invention may be employed in vaccine development in a way that has not been possible before. The improved method can be employed for analyzing the quality of antibody responses induced by different vaccine candidates speeding up vaccine development. Thus, the invention is important for vaccine research, development, prioritization and selection of vaccine candidates to proceed into clinical trials. This is exemplified here by using HIV-1 Env proteins but similar analysis can be done for any vaccine antigen. The differential method described herein is particularly useful.

Differential Assay

In one particularly preferred embodiment, the invention may be employed to monitor whether or not antibody secreting cells are present against a plurality of different epitopes. The epitopes may, in some instances, be part of the same antigen. In others the epitopes may be the equivalent region of the same antigen in different strains, where variant specific sequence changes are present. In others the epitopes may be different antigens specific to a plurality of pathogens.

The presence of the different epitopes may be measured separately or, in a preferred embodiment in the same reaction and in particular through the use of different fluorescent labels.

In one preferred instance, the invention may be used to map the presence or absence of antibody secreting cells producing antibodies against different epitopes within the same antigen and, preferably, may be used to compare the frequency of such cells between the epitopes.

In an especially preferred instance, the assay may also be used to monitor the hierarchy of antibody responses to viral antigens, particular HIV antigens and especially to the HIV-1 Env glycoproteins, particularly following vaccination or natural infection by using Env proteins as antigen probes.

US 2005/0220817 (U.S. application Ser. No. 11/126,797) and U.S. Pat. No. 7,105,655 (U.S. application Ser. No. 10/179,152) describe HIV Env proteins which are able to form stable trimers mimicking the Env protein in situ. Both are incorporated by reference and the modified proteins taught may be employed in the present application, as may other viral Env proteins generated using the same approach.

Thus, in one instance the protein employed may be a HIV-1 or HIV-2 envelope glycoprotein containing at least the coiled coil portion of the gp41 transmembrane envelope glycoprotein, wherein cysteine residues are introduced at residues adjacent to a d and e position of the coiled coil helix, and a gp120 glycoprotein or gp120 derivative, wherein the gp120 derivative contains multiple gp120 constant regions connected by variable regions and/or linker residues that permit potential turns in the polypeptide structure so the derivative maintains a conformation approximating that of wild type gp120, wherein at least a portion of one variable region has been deleted. In some instances, the gp120 derivative may lack portions of at least the V1, V2, C1 and/or C5 regions. Such proteins described in and U.S. Pat. No. 7,105,655 may, for instance, be employed.

In one embodiment a HIV-1 or HIV-2 gp125 monomer, referred to as a gp120 monomer, is employed wherein the gp120 monomers form a stable trimer, wherein the gp120 monomer has been modified from the wildtype sequence to encode a modified gp120 monomer, wherein the modified gp120 monomer maintains the overall three-dimensional structure of the wildtype gp120, wherein a portion of one variable region has been deleted, and wherein a trimeric motif has been added carboxyl to the gp120 monomer. Any such proteins described in, for instance, US 2005/0220817 may be employed.

The "differential assay", is exemplified herein using the HIV-1 clade B YU2 strain-based trimeric gp140-foldon glycoprotein probe, which was enzymatically labeled with three biotins per trimer at the C-terminus to map antibody secreting cell (in particular memory B cell) responses against specific regions of HIV Env. However, the method may be applied more widely to other antigens.

The 140-foldon-biotin is comprised of the HIV-1 external membrane protein, gp120, covalently fused to the ectodomain of the trimeric transmembrane protein, gp41, and is rendered highly trimeric by the addition of the trimer-forming foldon motif.

To develop the differential assay, this protein was engineered to contain selective deletions (for example each of the V1, V2 and V3 regions of gp120 or the gp41 portion was deleted) to map ASC responses directed against these specific regions while maintaining the overall integrity of and native structure of Env. A monomeric gp120-biotin probe was also made. All of these molecules have now been shown to function well to detect HIV Env specific memory B cells from splenocytes of Env-immunized mice. The gp140-foldon-biotin probe detects gp41-specific ASCs by determining the differential numbers of spots detected relative to the gp41-deleted gp120-foldon-biotin probe. The selectivity of the probes has been confirmed by using specific hybridomas. Biotinylated control proteins have been used as negative controls to show that the assay is highly specific. The differential assay method described here can be extended to selected HIV-1 Env point mutant variants to map fine ACS specificities and therefore represents a unique tool to understand complex polyclonal humoral immune responses.

The method described here can also be adapted to other HIV clades and lentiviral Env (ie SIV) or to monitor responses to other viral envelope glycoproteins such as influenza HA (esp H5 bird flu strains), hepatitis C or other viruses of interest to monitor vaccine development or to map the fine specificities of memory ASC cell responses to these viral surface proteins.

The HIV-1 envelope glycoprotein (Env) consists of a trimer of non-covalently associated gp120/gp41 heterodimers, which form the functional viral spike and mediate entry into CD4 and CCR5 receptor-positive host target cells. The exterior envelope glycoprotein, gp120, and the transmembrane glycoprotein, gp41, are the sole virally encoded targets for neutralizing antibodies (NAbs) on the surface of the virus and likely represent a critical immunogenic component for an effective prophylactic vaccine against HIV-1.

In attempts to elicit antibodies that would recognize the functional Env spike, soluble trimeric molecules containing full-length gp120 covalently linked to the gp41 ectodomain have been designed and may be employed (Binley et al., J Virol, 2000. 74(2): 627-643, Kim et al., AIDS Res Hum Retroviruses, 2005. 21(1): 58-67, Sanders et al., J Virol, 2002. 76(17): 8875-8889, Srivastava, et al., J Virol, 2003. 77(20): 11244-11259, Yang et al., J Virol, 2000. 74(12): 5716-5725, Yang et al., J Virol, 2002. 76(9): 4634-4642).

An incremental advance in NAb elicitation using soluble trimeric Env spike mimetics compared to the use of monomeric gp120 has been observed (Li et al., J Virol, 2006. 80(3): 1414-1426 and Yang et al., J Virol, 2001. 75(3): 1165-1171), but further improvements in trimer immunogen design are still needed both to better mimic the functional viral spike and to elicit broadly neutralizing antibodies.

Cleavage-defective Env trimers derived from the primary R5 isolate YU2 possessing a heterologous trimerization motifs derived either from T4 bacteriophage (fibritin) or from the transcription factor, GCN4, have been developed and examined in several small animals studies. The antibody response elicited by these and several other HIV-1 Env immunogens are relatively well-characterized at the serological level (serum antibody titers and serum neutralizing activity as determined using well-standardized HIV-1 neutralization assays). However, the responses elicited by most HIV-1 Env immunogens remain poorly characterized at the ASC cell level and the invention may be used to address that issue.

By using a series of antigen probes (such as the HIV-1 Env probes used in the Examples) that do or do not contain specific antigenic regions, the relative proportion of ASC cells recognizing certain classes of epitopes can be quantified. The invention thus provides a "Differential assay" based on the differential between two or more probes in terms of the numbers of antigen secreting cells that the probes detect.

In some instances the deleted region may be at least 1%, preferably at least 5% and even more preferably at least 10% of the antigen. In some instances several regions may be deleted in one test-molecule to help assess conformational epitopes that are not linear. A panel of test molecules may, for instance, comprise deletions encompassing the whole length of the test antigen. In others the deletions may correspond to functionally important domains or areas thought important in eliciting an immune response against.

Kits

The invention also provides a kit for carrying out a method of the invention. In particular, the present invention provides a kit for detecting or measuring Antibody Secreting Cells (ASCs) producing antibodies against an antigen, which kit comprises:
(i) a surface on which anti-Ig antibodies are immobilised; and
(ii) said antigen in labelled form.

Typically, the labelled antigen is provided in the form of a solution comprising the antigen.

In some instances, the kit may comprise a single labelled antigen, so ASCs producing antigen against just one antigen type are measured. In other instances, the invention also provides kits for detecting or measuring ASCs against a plurality of antigens. In one instance, such kits may comprise:
(i) a surface on which anti-Ig antibodies are immobilised; and
(ii) a plurality of antigens, where the antigens are differently labelled or tagged so that they are individually detectable.

In some instances, the kit may comprise at least two, three, four, five, or six such labelled or tagged antigens, up to four, five, or ten such differently labelled antigens or from two to ten, from four to ten or from four to six such differently labelled antigens.

The kit may also comprise means for detecting the labelled or tagged antigen, including any such means described herein.

The invention also provides a kit for carrying out a method of the invention, which kit comprises a kit for determining the specificity of antibodies generated in response to a pathogenic agent, tumour cell, allergen or autoantigen the kit comprising:

(i) a surface on which anti-Ig antibodies are immobilised;
(ii) a first labelled antigen; and
(iii) a second labelled antigen, wherein the first and second labelled antigen are different molecules, or fragments of molecules, derived from the same pathogenic agent, allergen, autoantigen or tumour antigen. In one preferred instance, the kit determines the specificity of antibodies generated in response to a pathogenic agent or tumour cell.

The kit may additionally comprise medium for the cells and/or washing buffers to be used in the detection steps.

The kit may also comprise controls, such as positive or negative controls. The kit may also comprise a means to take a sample containing cells from a subject, such as a blood sample. The kit may comprise a means to separate ASCs, particularly mononuclear cells or B-cells from a blood sample.

The labelled antigen may be any of those described herein and any of the detection methods referred to herein. Any of the combinations of reagents described herein may be present in the kit. The kit may include instructions specific to any of the methods described herein.

The following Examples illustrate the invention.

EXAMPLES

Example 1: Tests with Hybridoma Cells

Three different mouse anti-human hybridomas were used to test the principle of coating the ELISpot plates with anti-Ig antibodies and using a labelled antigen to detect the antibodies of interest (the alternative assay) and to compare the new method with the conventional ASC assay method in which the plates are coated with antigen and labelled anti-Ig antibodies are used to detect the antibodies bound to the immobilized antigen. The three hybridomas produced antibodies reactive with IgE, IFN-γ and IL-2 of human origin, respectively.

The proteins (IgE, IFN-γ and IL-2) were either used for coating as in the conventional B-cell ELISpot or biotinylated forms of the proteins were used as detection reagents in the alternative assay. The proteins were biotinylated according to a regular protocol for biotinylation.

In brief, ELISpot plates with PVDF membranes (MAIPSWU®, Millipore®) were first preactivated by incubating with 50 μl 70% ethanol for 2 min, followed by washing with sterile deionized water. For the conventional ELISpot assay, the respective antigen was added at different concentrations. IgE was used at concentration of 15 μg/ml and IL-2 at 10 μg/ml. For the alternative assay, the same volume (100 μl/well) of affinity purified goat anti-mouse IgG (Mabtech) diluted in sterile PBS (15 μg/ml) was added. The plates were left to coat overnight at +4° C. after which any unbound protein was removed by washing and the wells were blocked/equilibrated by incubating for 1 hour with cell culture medium (DMEM with 8% fetal calf serum (FCS)). Varying numbers of cells were then added (100 μl/well) and incubated overnight in an 37° C. incubator with 5% $CO_2$.

After incubation, cells were removed by washing in an ELISA washer (6×200 Biotinylated anti-mouse IgG was added to the antigen coated wells (100 μl/well; 1 μg/ml) and biotinylated antigens were added to the anti-IgG coated wells at different concentrations. A range of concentrations were used, but in the results depicted in FIG. 1 biotinylated IgE was used a concentration of 0.5 μg/ml and IL-2 at 0.05 μg/ml.

After 2 hours incubation, Streptavidin-ALP (100 μl/well; 1000× dilution, Mabtech) was added and incubated for 1 hour. After further washing, the substrate 5-bromo-4-chloro-3-indolyl phosphate/nitro blue tetrazolium (BCIP/NBT) was added and incubated until distinct spots were visible. The plates were then washed extensively in tap water and left to dry before being inspected and evaluated in an ELISpot reader (AID, Strassberg). The results are shown in FIG. 1 for IgE and IL-2.

As seen from FIG. 1, the results obtained using plates coated with anti-IgG followed by detection with biotinylated antigen were superior to plates that were coated with antigen as in the conventional ASC ELISpot. The difference related both to the quality of the spots (more distinct and easier to evaluate) and the effectiveness of detection with more spots being detectable. Similar results as those obtained with IgE was also observed for IFN-γ (data not shown).

Notably, for IL-2, no spots could be seen when the protein was used to coat the plates whereas spots were readily detectable when using biotinylated IL-2 for detection. These results, which were consistent in several experiments, suggest that the binding of IL-2 to the ELISpot plates may lead to a destruction and/or masking of the relevant epitope when the antigen is bound to the plate. Alternatively IL-2 is not efficiently bound to the plate. The method of the invention does not suffer from such disadvantages.

In many cases, the antigens used are only available in small amounts or the price may be prohibitive. The amount of antigen required in the two assays was therefore compared. The antigens IFN-γ, and IgE were used at different concentrations both for coating and as a biotinylated detection reagent. Results showed that biotinylated antigen could be used at substantially lower concentrations (approx. 20-200 times) as compared to using the antigen for coating.

Figure 2:
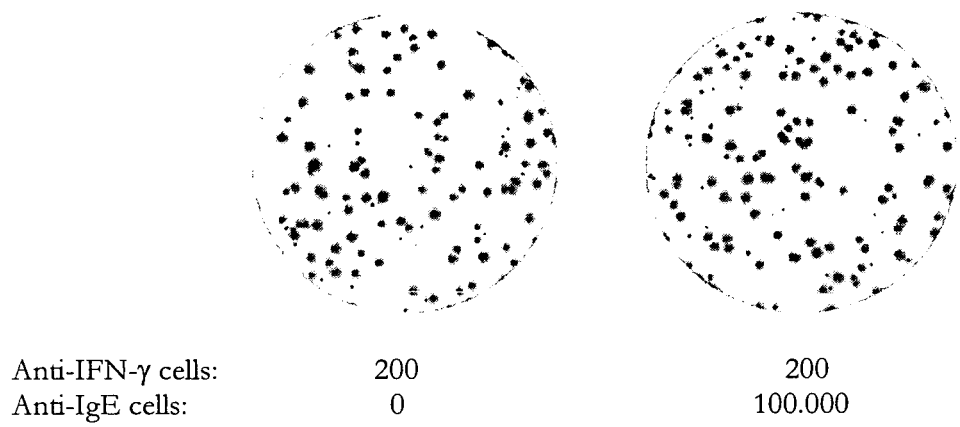
FIG. 2 shows the results of ELISpot analysis of IFN-γ producing cells in the absence or presence of cells producing irrelevant antibody (anti-IgE). Plates were coated with goat anti-mouse IgG and hybridoma cells producing anti-IFN-γ antibodies were added (200 cells/well) in the presence or absence of anti-IgE producing hybridoma cells (100,000 cells/well) and cells were cultured overnight. Detection was made with biotinylated IFN-γ (0.1 μg/ml; 100 μl/well).

The antibodies that are produced need to be efficiently captured at the site of the producing cells. One potential weakness of the alternative approach using plates coated with anti-Ig antibodies is that capture of the antibodies of interest may be negatively affected by the presence of an excess of ASCs producing other antibodies which compete for binding. To address this issue, the alternative assay was repeated using similar numbers of antigen specific hybridoma cells as before but in the presence of increasing numbers of cells producing irrelevant antibodies. For this experiment, the two hybridomas producing IFN-γ and IgE antibodies were used and an excess number of anti-IgE producing cells were added to wells for analyzing IFN-γ producing cells and vice versa. As seen in FIG. 2, no significant effect on the number of IFN-γ-specific spots was seen when adding up to 100,000 irrelevant hybridoma cells (anti-IgE). The same was seen when IgE spots were analyzed in the presence of excess numbers of anti-IFN-γ producing cells (data not shown). Cell numbers higher than 100,000 cells/well were not used as this may result in multiple layers of cells in the wells which may in itself affect detection (hybridoma cells are bigger than, for example, freshly isolated PBMC that can be used at 400,000 cells/well).

Example 2: Tests with Immunized Mouse Cells

The alternative assay method was also compared to the conventional method using freshly isolated spleen cells from mice immunized with ovalbumin. Experiments were performed similarly to above using either ovalbumin coated to the ELISpot plates (15 μg/ml; 100 μl/well) and biotinylated goat anti-mouse Ig for detection (i.e. conventional ELISpot) or wells coated with goat anti-mouse Ig (15 μg/ml; 100 μl/well) and biotinylated ovalbumin (0.5 μg/ml; 100 μl/well) for detection (i.e. alternative assay). In the last step Streptavidin-enzyme (alkaline phosphatase (ALP) or horseradish peroxidase (HRP)) was added followed by development with the appropriate substrate (BCIP/NBT and tetramethylbenzidine (TMB), respectively). As the frequency of cells producing specific antibodies are here much lower, more cells were used in the wells (200,000 cells/well).

Figure 3:
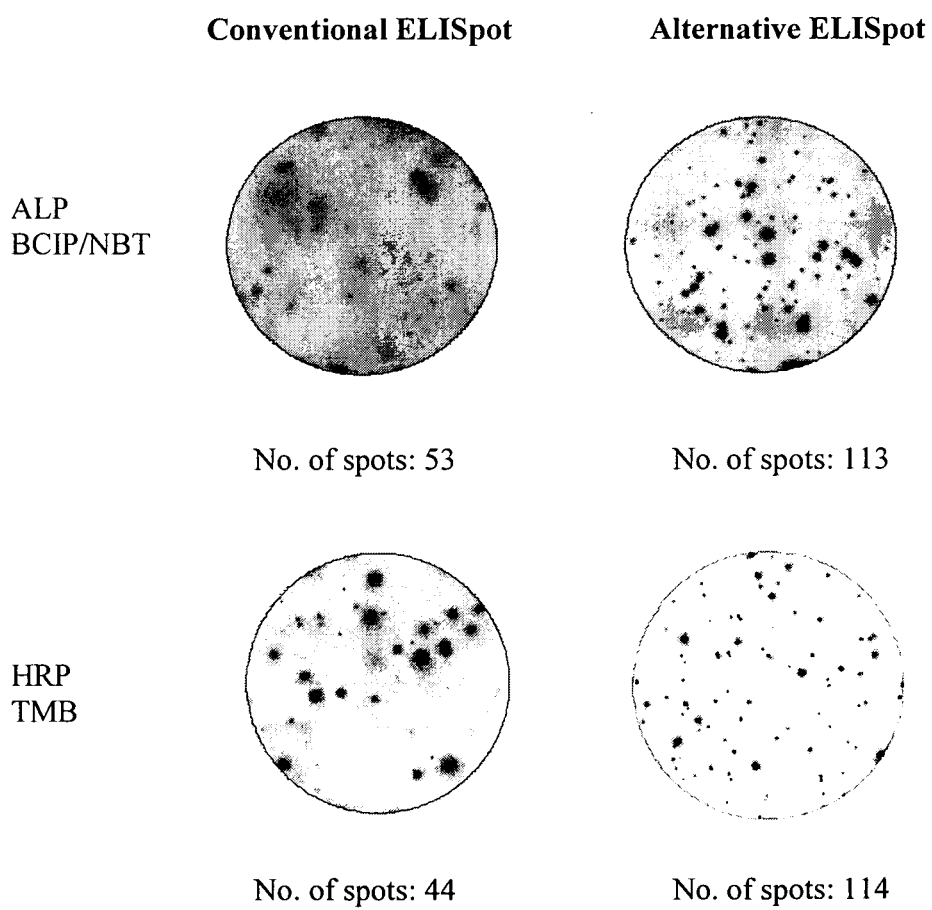
FIG. 3 shows a comparison between the conventional and alternative ELISpot using spleen cells from mice immunized with ovalbumin.

As seen in FIG. 3, and in line with the previous observations, more spots were observed when using biotinylated antigen for detection and the spots were of higher quality. Similar results were observed with both Streptavidin conjugates (i.e. ALP and HRP).

Example 3: Tests with Human Cells from Vaccinated Individuals

To further demonstrate the general utility of the alternative approach, peripheral blood mononuclear cells (PBMC) were prepared from individuals before and after vaccination with the cholera toxin vaccine, DUKORAL®. This vaccine is administered orally and designed to give good mucosal protection with induction of Cholera toxin specific IgA and IgG antibodies.

Figure 4:
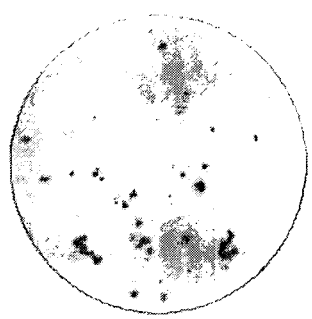
FIG. 4 shows IgA responses to the cholera toxin vaccine DUKORAL® using the conventional and alternative ASC assays of the invention. In the conventional ELISpot, plates were coated with 5 μg/ml; 100 μl/well of the cholera toxin whereas in the alternative assay plates were coated with goat anti-human IgA antibodies (15 μg/ml; 100 μl/ml). PBMC from blood collected before vaccination and 7 days after a second vaccination were added to the coated plates (200,000 cells/well) and incubated overnight. Spots were then revealed by the addition of 1 μg/ml biotinylated goat anti-human IgA (conventional assay) or 0.5 μg/ml biotinylated cholera toxin (alternative assay) followed by Streptavidin-ALP and the substrate 5-bromo-4-chloro-3-indolyl phosphate/nitro blue tetrazolium (BCIP/NBT).
Figure 4:
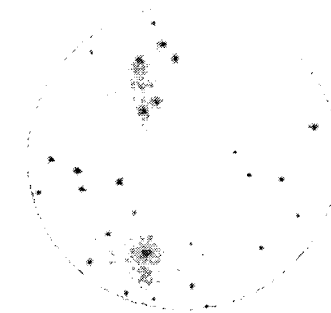

As before, the antigen (the vaccine was used as antigen source) was either coated to ELISpot plates or was biotinylated and used for detection. As seen in FIG. 4, no spots were observed before vaccination whereas similar numbers of specific IgA spots were observed with both methods after vaccination. As earlier and in spite of any optimization (biotinylation was performed under suboptimal conditions due to shortage of antigen) spots were of significantly better quality and more easily evaluated when biotinylated antigen was used for detection compared to when the antigen was used for coating.

In addition to the cholera toxin, cells from influenza vaccinated individuals were also tested for specific IgG producing cells with a similar difference between the conventional and alternative assay (data not shown).

Example 4: Background

Figure 5:
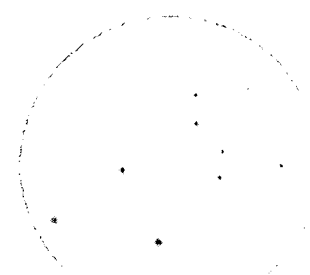
FIG. 5 is a comparison of background reactivities in the conventional and alternative assays. ELISpot plates were blocked with BSA and spleen cells (200,000 cells/well) were incubated overnight. The plates were "developed" by the addition of biotinylated anti-mouse Ig (conventional ELISpot) or biotinylated ovalbumin (alternative assay).

The propensities of the two assays to generate background were also compared. For this purpose spleen cells from non-immunized mice or human PBMC were tested using ELISpot plates that had not been coated but only blocked with BSA. After incubation overnight cells were removed and the plates were "developed" by adding biotinylated anti-mouse Ig or anti-human Ig (conventional ELISpot) or biotinylated antigen (alternative assay). As illustrated in FIG. 5 with human PBMC (200,000 cells/well), spots could be detected in the conventional assay but not in the alternative assay. Spot numbers varied between different PBMC samples but were observed in most donors. Similar results were obtained with mouse spleen cells (data not shown).

These background spots could represent a real reactivity to the BSA used for blocking or may originate from cells secreting generally "sticky" antibodies with the capacity to bind non-specifically to the plates. However, the existence of ASCs producing this kind of non-specific, sticky antibodies has been observed previously by means of other assays and so this may also be the case here.

Independent of the underlying reason for their presence, background spots may create significant problems when using the conventional ASC ELISpot. In particular, if the test were to be applied in diagnostic situations that are based on whether a person has or has not been exposed to a certain infectious agent any background spots may complicate the evaluation and increase the risk of misinterpretation. Therefore, the lack of background spots in the alternative assay may represent a major advantage making it particularly useful for diagnostic applications.

Example 5: Detection of Antibodies to HIV Env

HIV-1 Env specific ASC responses were analyzed using hybridoma cells and splenocytes from immunized mice. The HIV-1 envelope glycoproteins are some of the best-characterized viral glycoproteins described so far.

A large body of previous data has shown that antibodies against HIV-1 Env can be divided in different subclasses including, for example, (i) antibodies directed against variable regions V1, V2 and V3 of gp120, (ii) monomer-specific antibodies that bind surfaces of the protein that are not exposed on the functional trimeric spike, (iii) trimer-specific antibodies that bind across the individual monomers in the trimer but that do not bind monomeric gp120, (iv) antibodies directed against the CD4 binding site (v) antibodies directed against the co-receptor binding site, (vi) antibodies directed against different regions of gp41, and (probably more rare) antibodies targeting epitopes containing N-linked glycans on the outer face of gp120. Most of these classes of antibodies are not capable of broadly neutralizing primary circulating HIV-1 isolates, either because they bind to determinants that are very strain-restricted (such as the highly variable regions), or because they have been elicited against soluble or defective antigenic material and therefore are directed against epitopes that are not accessible on the functional trimeric virus spike.

HIV-1 Env is also a highly relevant antigen in terms of human medicine today as there is an urgent need to develop improved vaccine candidates against HIV-1 and to better understand HIV-1 Env-directed ASC responses. The availability of a highly specific and sensitive ASC ELISpot assay coupled with the possibility of using the probes developed for the differential ELISpot described below will elevate the analysis of vaccine-induced ASC responses to a new level.

Circulating strains of HIV-1 are notoriously difficult to neutralize as the virus has evolved many immune evasion strategies, such as highly variable loop structures, a densely glycosylated outer face that shields antibody binding efficiently, exposure of decoy epitopes, as well as poorly accessibly antibody epitopes against the conserved receptor binding site. So far, efforts to develop a vaccine against HIV-1 have proven to be extremely difficult and current Env-based immunogens stimulate antibodies with limited neutralization breadth. While vaccine-induced antibodies usually bind gp120 in conventional ELISA analysis, they do not neutralize virus infection. However, a handful of monoclonal antibodies from HIV-1 infected individuals have been isolated, such as those that bind the CD4-binding site of gp120 or the membrane-proximal domain of gp41, and they are capable of broad neutralization. It is therefore highly relevant to develop tools that will allow a more detailed analysis of the polyclonal B cell response elicited during vaccination or infection to better understand how broadly neutralizing antibodies can be elicited.

Env-specific mouse hybridoma cells (5D4-F7) were obtained from J. Hoxie and were grown in DMEM containing 10% fetal calf serum (FCS), L-glutamine and antibiotics. In the immunization studies, 7 week old male Balb/C mice were immunized subcutaneously two or three times, two weeks apart, with 10 µg of HIV-1 YU2 gp140-F (10 mice) or as a control group, 10 µg B-gal (5 mice) in combination with 10 µg of the adjuvant AbISCO®-100 (Isconova, Uppsala, Sweden).

Single cell suspensions were prepared by passing the tissue through a nylon mesh. Red blood cells were lysed with a hypotonic ammonium chloride solution and washed in PBS. The cells were resuspended in complete RPMI-medium containing 5% FCS, 50 µM B-Mercaptoethanol, L-glutamine and antibiotics at a final concentration of $1\times10^7$ cells/ml and then further diluted in three fold dilutions according to the ASC ELISpot layout down to $1.2\times10^5$ cells/ml.

Biotinylated, trimeric, cleavage-defective gp140 (gp140-F-bio) was derived from gp140Δ683(−/FT) which consists of HIV-1 YU2 Env amino acids 1 to 683 fused to the T4 phage fibritin trimerization domain as described in (Yang2002). The gp140Δ683(−/FT) sequence was modified by addition of the sequence encoding the Avitag signal for biotinylation (GLNDIFEAQKIEWHE—SEQ ID No:1) and subcloned into pCDNA3.1(−).

The trimeric gp120 (gp120-FT-His-Bio) was derived from gp140-FT-His-Bio as described above. The amino acid residue from 512 to 683 was deleted and also the linker sequence GGSG was introduced followed by the foldon motif, Histidine tag and the biotinylation signal as present in gp140-FT-Bio. The monomeric gp120 (gp120-His-Bio) was made by removing the foldon domain from the trimeric gp120-FT-His-Bio. Furthermore, trimeric delV3 gp120 (delV3gp120-FT-His-Bio), was derived by simply deleting the amino acids from 302 to 324, from the trimeric gp120 (gp120-FT-His-Bio). It was further modified by deleting the amino acids from 126 to 197 to make delV1, V2, V3 gp120 (delV1, V2, V3gp120-FT-His-Bio). The delV1, V2 gp120 (delV1, V2gp120-FT-His-Bio) was constructed by deleting the amino acids from 126 to 197 of trimeric gp120 (gp120-FT-His-Bio).

The resulting plasmid was used to transfect 293 freestyle cells at a density of 1.2×106/ml using 293 fectin (Invitrogen) according to the manufacturer's protocol. After 4 days in culture in shake flasks at 37° C. The supernatant was collected four days after transfection. Following collection, all supernatants were centrifuged at 3,500 g to remove cells or cell debris, filtered through a 0.22 mm filter and supplemented with CompleteT®, EDTA-free protease inhibitor cocktail. The gp140-F trimers were purified by lentil lectin affinity chromatography followed by chelation chromatography over a Ni-charged column (GE Health Care). All the gp120 proteins were purified through 17b antibody affinity column.

Biotin ligase Bir A (Avidity, Denver, Co) was used to biotinylate specifically at the Avitag sequence, distal to the relevant Env epitopes. The biotinylation of the gp140-F trimers was confirmed by ELISA using Strepavidin-HRP (Sigma). The antigenic structure was not affected by biotinylation, as demonstrated by binding of monoclonal antibodies b12, F105, and 17b with or without soluble CD4 (unpublished data).

96-well MultiScreen-IP filter plates (Millipore®, Bedford, Mass., USA) were pre-treated with 70% EtOH and washed 3 times in PBS, before being coated with either 0.54/well of insect cell (S2) produced gp120 monomers for the conventional ELISpot, or with 14/well of unconjugated goat anti-mouse IgG (Mabtech, Nacka strand, Sweden) for the alternative and the total IgG ELISpot. The plates were incubated overnight at 4° C. Two hours before addition of the cells, the plates were blocked with complete RPMI-medium at 37° C. for 2 hours and then washed 5 times in PBS. Cells derived from immunized mice or hybridoma cells were added to the wells in 3-fold dilutions, starting at 5000 cells/well for hybridoma cells, $1\times10^6$ cells/well for splenocytes and $3.3\times10^5$ cells/well for draining lymph node cells. Plates were then incubated for 12 hrs at 37° C. Before detection of spots, the cells were first removed by washing the plates 6 times in PBS/0.05% Tween 20.

For the conventional ELISpot, 0.1 µg/well of a biotinylated goat anti-mouse IgG (Mabtech, Nacka strand, Sweden) was added in blocking buffer (0.05% Tween 20/1% FCS in PBS) and for the alternative assay, 0.2 µg/well of biotinylated protein (variants of Env or B-gal as a control) was added in blocking buffer. Biotinylated antibody and protein were incubated for two hrs at room temperature. Plates were then washed 6 times in PBS before 100 µl of ALP-conjugated streptavidin diluted 1:5000 in PBS (Mabtech, Nacka strand, Sweden) was added. Plates were incubated for 1.5 hrs at room temperature and then washed 6 times in water. 100 µl of BCIP/NBT-plus substrate was then added and incubated for approximately 10 minutes at room temperature. Plates were then washed extensively in tap water and allowed to dry. Spots were counted in ELISpot reader (ImmunoSpot®, Cellular Technology Ltd, Cleveland, Ohio).

Figure 6:
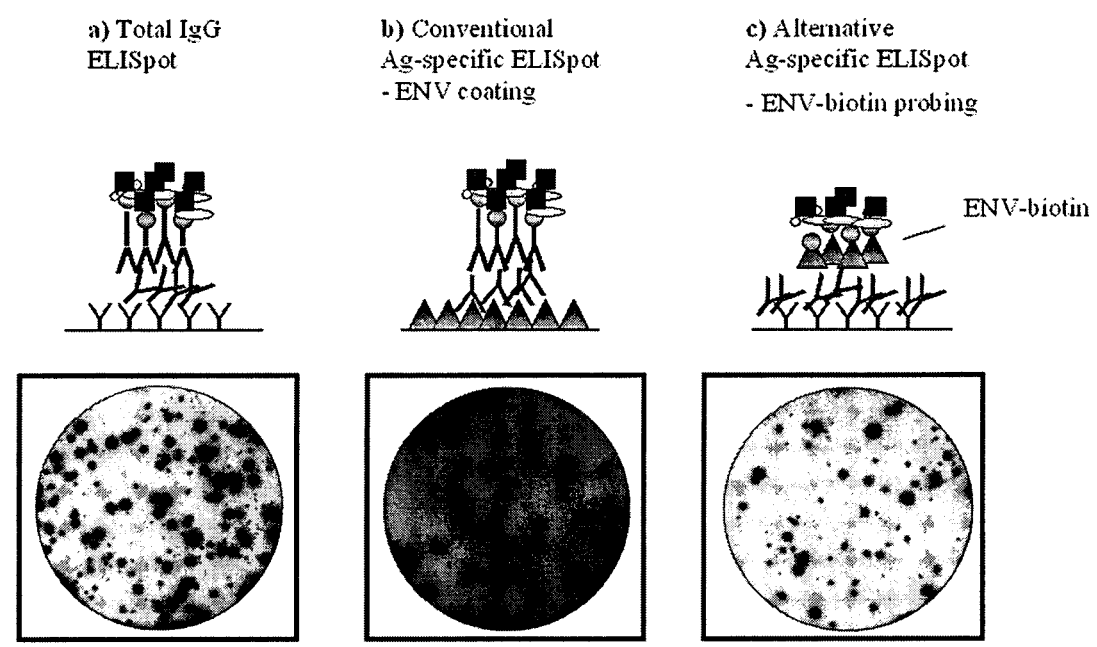
FIG. 6 includes schematic drawings of the total IgG (FIG. 6a), conventional (FIG. 6b) and alternative (FIG. 6c) assays and shows ELISpot images of developed wells from the three different approaches of the assay.

ELISpot images of developed wells from the three different approaches of the assay are shown in FIG. 6. The alternative ELISpot approach allows for the visualization of well-defined spots highly comparable to the spots formed in the total IgG assay.

Figure 7:
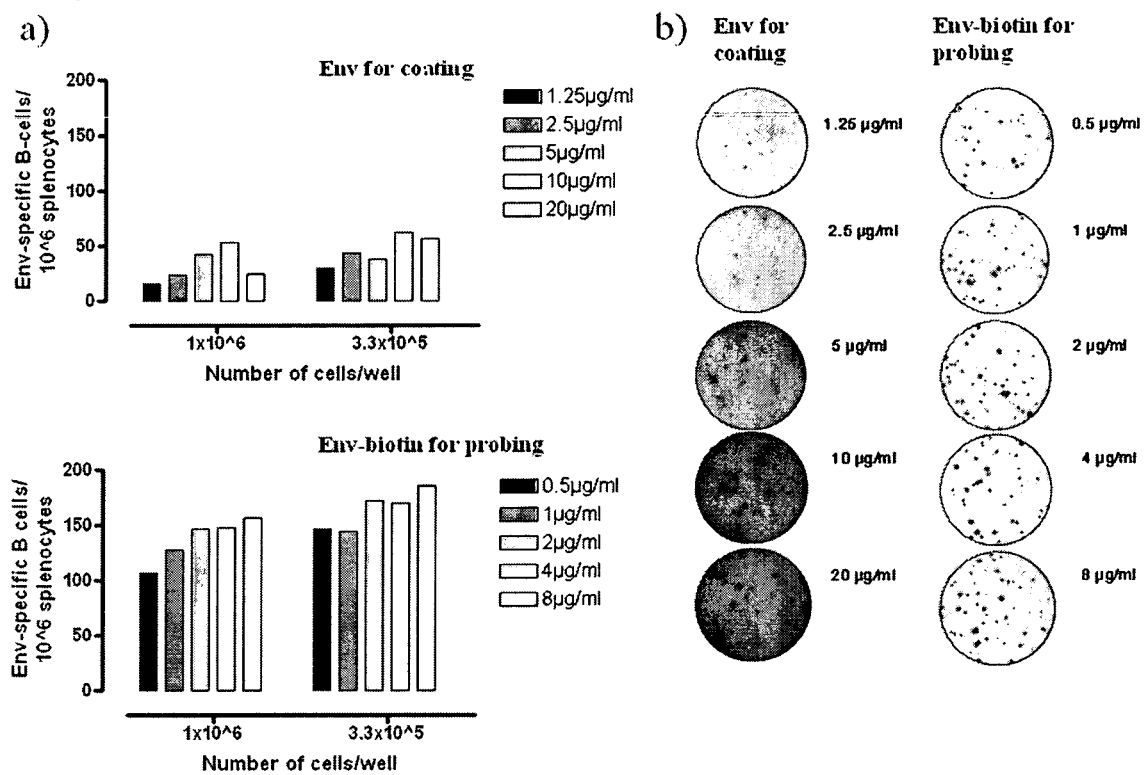
FIG. 7 shows the results from the titration of the protein for the conventional ELISpot (Env for coating) and the alternative assay (Env-biotin for probing) using splenocytes from an Env immunized mouse (FIG. 7a) and ELISpot images from the wells with $3.3 \times 10^5$ cells/well in the same experiment (FIG. 7b).

The results from the titration of the protein for the conventional ELISpot (Env for coating) and the alternative assay (Env-biotin for probing) using splenocytes from an Env immunized mouse are shown in FIG. 7a and ELISpot images from the wells with $3.3\times10^5$ cells/well in the same experiment are shown in FIG. 7b. The results show that the alternative assay allows for the usage of less protein and the formation of well-defined spots with less background compared to the conventional assay where wells are coated with the protein before cells are added.

Figure 9:
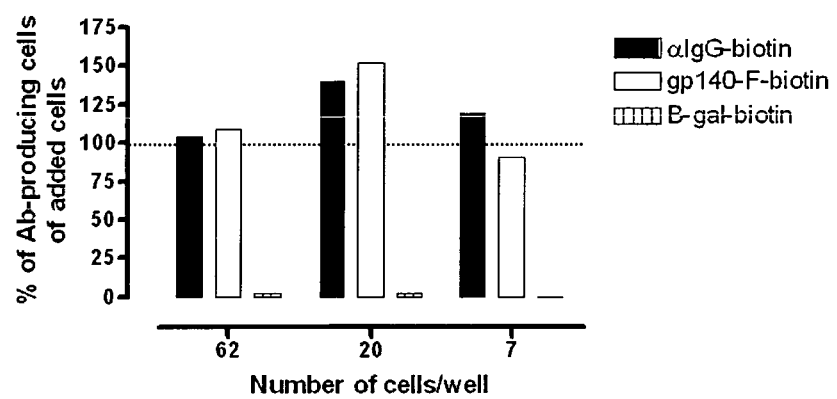
FIG. 9 shows the sensitivity and specificity of the alternative assay using Env-specific mouse hybridoma cells by comparing detection of total IgG producing cells and Env-specific B cells. Close to 100% of the added hybridoma cells are detected in both the total IgG ELISpot and the antigen-specific ELISpot.

Results of the alternative assay on Env-specific mouse hybridoma cells are shown in FIG. 9. Close to 100% of the added hybridoma cells were detected in both the total IgG ELISpot and the antigen-specific ELISpot, which shows high specificity of the assays. Both assays showed similar numbers of antigen secreting cells (ASCs), which suggests similar sensitivity in the two assays. Very low background was detected with the biotinylated control protein, which demonstrates high specificity.

Example 6: Differential Assay

By using a series of carefully designed HIV-1 Env probes that do or do not contain specific antigenic regions, the relative proportion of ASCs recognizing certain classes of epitopes can be quantitated. This "Differential assay" is based on the differential between two or more probes in terms of the numbers of antigen secreting cells that the probes detect.

Figure 8:
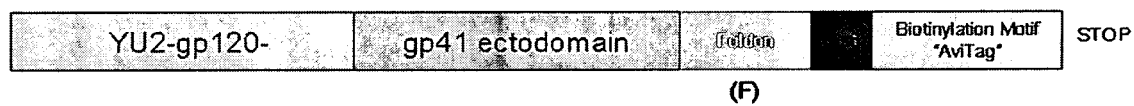
FIG. 8 shows schematic illustrations of the Env construct used for the production of biotinylated HIV-1 gp140-F (a) and of the trimeric gp140 molecule showing the biotinylation site in the distal part of the protein (b).
Figure 8:
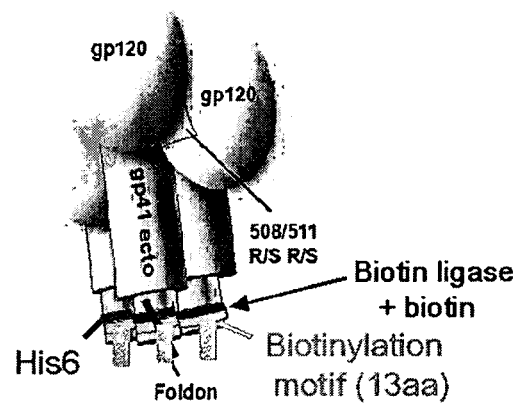

The Env construct used for the production of biotinylated HIV-1 gp140-F and the trimeric gp140 molecule are depicted in FIG. 8. The biotinylation site is in the distal part of the protein so that biotinylation of the protein is well controlled and specific, which is of particular importance when using the probes for the detection of conformation-dependent Env-specific antibodies.

Figure 10:
FIG. 10 includes a panel of the proteins used for immunization and/or probing in the alternative Env-specific assay and for differential analysis of antibody responses against Env (a) and the results of SDS-PAGE analysis of the Env probes using under reducing conditions, verifying the correct sizes and purity of the different biotinylated Env-proteins.
Figure 10:
Figure 10:
Figure 10:
Figure 10:
Figure 10:
Figure 10:
Figure 10:
Figure 10:
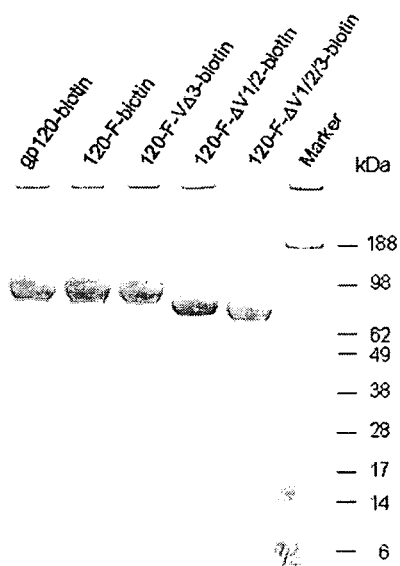

The panel of proteins used for immunization and/or probing in the alternative Env-specific ELISpot and for differential analysis of antibody responses against Env are described in FIG. 10a. The 140-F-biotin probe was prepared as described above and the trimeric gp120 (gp120-F-biotin) was derived from gp140-F-biotin. The amino acid residues from 512 to 683 were deleted and the linker sequence GGSG was introduced followed by the fibritin trimerization motif, Histidine tag and the biotinylation signal as present in gp140-F-biotin. The monomeric gp120 (gp120-biotin) was made by removing the fibritin trimerization domain from the trimeric gp120-F-biotin. Furthermore, trimeric V3-deleted gp120 (gp120-F-ΔV3-biotin) was derived by deleting the amino acids from 302 to 324, from the trimeric gp120 (120-F-biotin). It was further modified by deleting the amino acids from 126 to 197 to make V1, V2, V3 deleted gp120 (gp120-F-ΔV 1/2/3-biotin). The V1 and V2 deleted gp120 (gp120-F-ΔV 1/2-biotin) was constructed by deleting the amino acids from 126 to 197 of trimeric gp120 (120-F-biotin).

The resulting plasmids were used to transfect 293 freestyle cells at a density of $1.2 \times 10^6$ cells/ml using 293 fectin (Invitrogen) according to the manufacturer's protocol. After 4 days in culture in shake flasks at 37° C. following transfection, the supernatant was collected four days after transfection. Following collection, all supernatants were centrifuged at 3,500 g to remove cells or cell debris, filtered through a 0.22 mm filter and supplemented with CompleteT®, EDTA-free protease inhibitor cocktail. The gp140-F trimers were purified by lentil lectin affinity chromatography followed by chelation chromatography over a Ni-charged column (GE Health Care). The gp120 proteins were purified through 17b antibody affinity column.

Biotin ligase Bir A (Avidity, Denver, Co) was used to biotinylate specifically at the Avitag sequence, distal to the relevant Env antibody epitopes. The biotinylation was confirmed by ELISA using Strepavidin-HRP (Sigma). The antigenic structure was not affected by biotinylation, as demonstrated by binding of monoclonal antibodies b12, F105, and 17b with or without soluble CD4.

The Env probes were analysed using SDS-PAGE under reducing conditions to verify the correct sizes and purity of the different biotinylated Env-proteins and the results of this analysis are shown in FIG. 10b.

Figure 11:
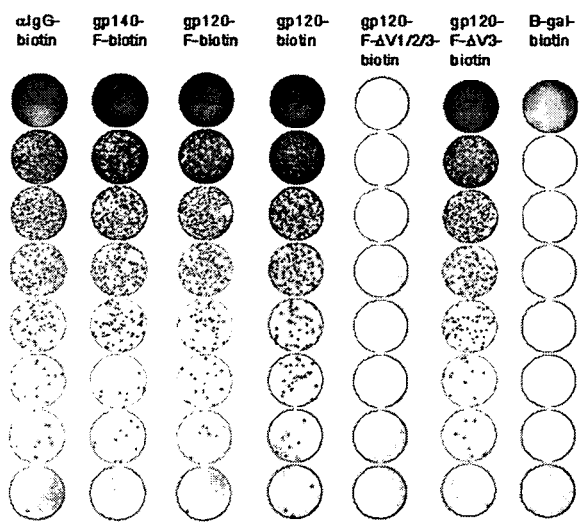
FIG. 11 shows ELISpot images of a differential ELISpot on Env-specific mouse hybridoma cells for verification of antibody specificity (a) and a diagram of the same experiment showing the percentage of detected cells out of total cells added/well (b).
Figure 11:
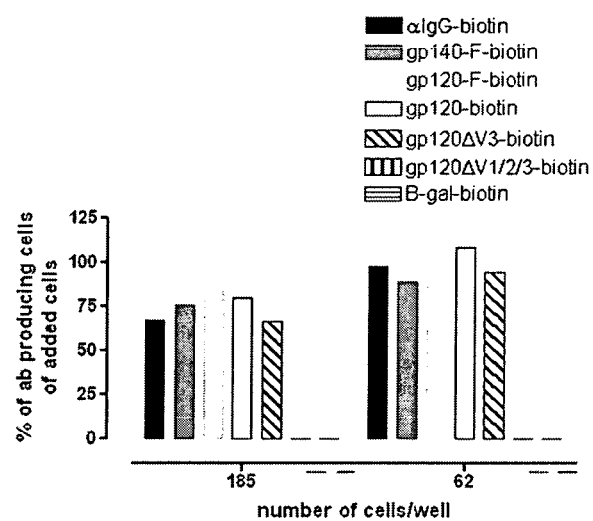

The alternative assay and total Ig assay were carried out using the different Env probes. The results of the differential ELISpot for verification of antibody specificity of antibodies produced by Env-specific mouse hybridoma cells are shown in FIG. 11. The biotinylated Env probe lacking variable loop 3 (gp120-F-ΔV3-biotin) bound to antibodies produced by the hybridoma cells, but the biotinylated Env probe lacking all three variable loops (gp120-F-ΔV1/2/3-biotin) did not. Therefore, the cells are producing antibodies directed towards the variable loops 1 and 2. The fact that no background spots were observed with 120-F-ΔV1/2/3-biotin indicates the high specificity of the probes.

Figure 12:
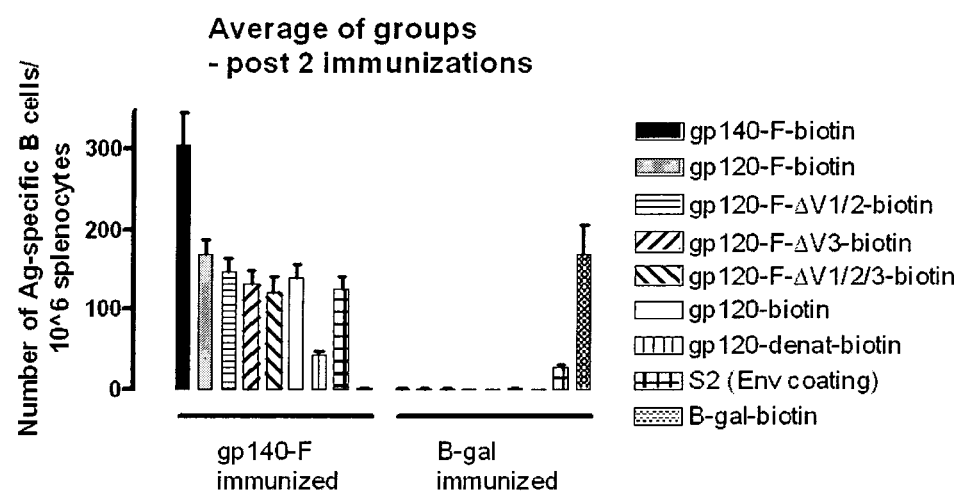
FIG. 12 shows the results of a differential ELISpot in gp140-F- and B-gal immunized mice, 10 and 5 animals per group respectively.

The results of a differential ELISpot using cells from gp140-F- and B-gal immunized mice, 10 and 5 animals per group respectively, are shown in FIG. 12. This experiment displays the specificity of the alternative assay. Very low background was observed using cells from the control (B-gal immunized) mice, compared to the conventional ELISpot, where background spots were detected in the control mice. It is also apparent that the deleted biotinylated proteins pick up fewer antigen-secreting cells than the gp140-F probe. This illustrates the differential that can be calculated upon comparing the probes.

Figure 13:
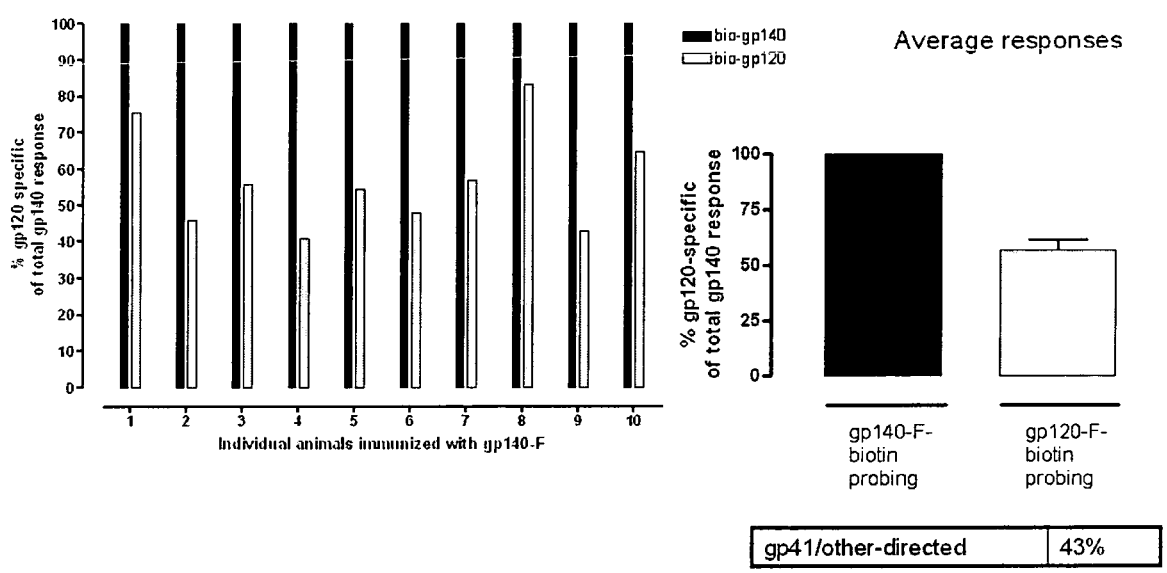
FIG. 13 shows the B cell responses directed against anti-gp41 calculated by analyzing the differential between gp140-F-biotin and gp120-F-biotin. The gp140 response was set to 100%. A significant fraction of the antibody response appears to be directed against gp41 or other gp140-F specific sites.

B cell responses directed against anti-gp41 were calculated by analyzing the differential between gp140-F-biotin and gp120-F-biotin and the results are shown in FIG. 13. The gp140 response was set to 100%. A significant fraction of the antibody response appeared to be directed against gp41 or other gp140-F specific sites. These data demonstrate quite clearly that the concept of the "differential assay" works well.

Figure 14:
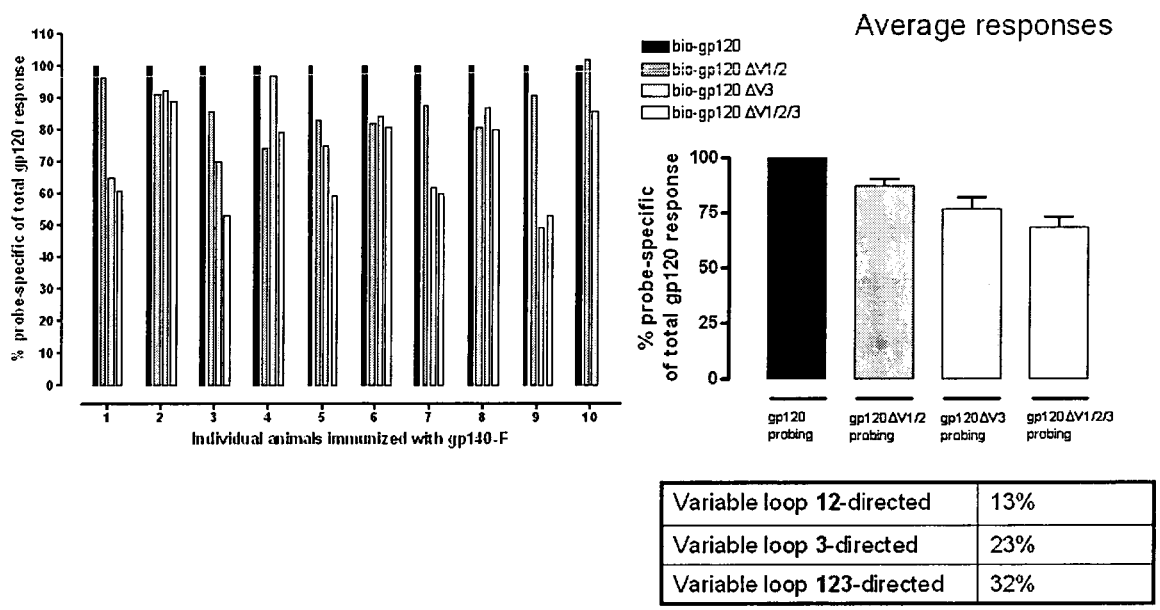
FIG. 14 shows the B cell responses directed against the variable region 1+2 (V1/2), variable region 3 (V3) and variable region 1+2+3 (V1/2/3) of gp120 calculated by analyzing the differential between gp120-F-biotin and gp120-F-ΔV1/2-biotin, gp120-F-ΔV3 and 120-F-ΔV1/2/3-biotin. The response against gp120-F-biotin was set to 100%.

B cell responses directed against the variable region 1+2 (V1/2), variable region 3 (V3) and variable region 1+2+3 (V1/2/3) of gp120 were calculated by analyzing the differential between gp120-F-biotin and gp120-F-ΔV1/2-biotin, gp120-F-ΔV3 and 120-F-ΔV1/2/3-biotin. The results are shown in FIG. 14. The response against gp120-F-biotin was set to 100%. This, like the results shown in FIG. 13, shows the potential of calculating different specificities of antigen secreting cells after immunization or natural infection, which could vary greatly upon using different antigens and/or analyzing samples at different times post immunization or infection.

Example 7: Two Colour Assay

Fluorospot staining was performed using two types of hybridoma cells. One of the hybridomas used produced antibodies to human IFN-gamma and the other irrelevant antibodies. The cells were then added in different numbers and proportions to plates coated with anti-mouse IgG and incubated overnight.

All cells producing antibodies (i.e. both the cells producing anti-IFN-gamma antibodies and those producing irrelevant antibodies) were then detected by the addition of fluorochrome conjugated anti-mouse IgG (green). The cells producing anti-IFN-gamma antibodies were specifically detected by the addition of biotinylated IFN-gamma together with fluorochrome conjugated Streptavidin (red).

Figure 18:
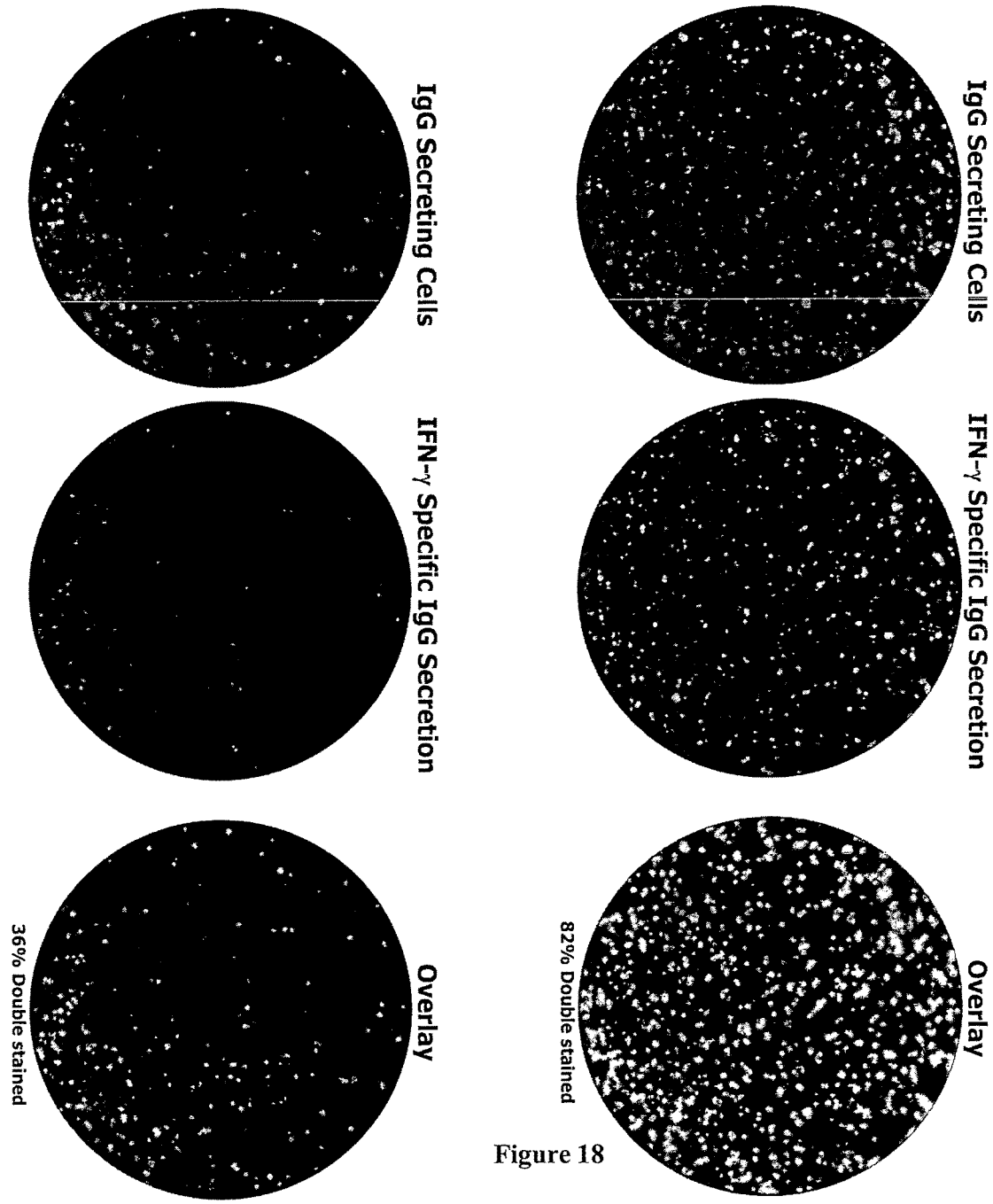
FIG. 18 shows the results of Fluorospot using two types of hybridoma cells with dual colour staining using a fluorochrome conjugated anti-mouse IgG (green) and biotinylated IFN-gamma together with fluorochrome conjugated Streptavidin (red). Results are shown for each fluorochrome individually and also double staining for both.

The overlay of the two results showed some spots which were yellow (i.e. they were stained with both red and green) while the cells producing irrelevant antibodies were simply green. (FIG. 18).

Example 8

Following on from the work described in Examples 5 and 6, in order to further illustrate the efficacy of the invention, the evolution of the Env-directed B cell response in adult BALB/c mice was investigated following two and three immunizations with gp140-F trimers (groups 1 and 3) or control protein (groups 2 and 4) in adjuvant. Spleens and sera were harvested 3 days after the second immunization (groups 1 and 2, post 2 immunizations) or 3 days after the third immunization (groups 3 and 4, post 3 immunizations).

The serological response after two immunizations was confirmed to be similar in groups 1 and 3, as shown by the Env-specific IgG titers in sera 3 days after the second immunizations (FIG. 15A), allowing a direct comparison between the two groups in the subsequent analysis. As expected, the circulating Env-specific IgG titer in group 3 was increased after the third immunization (FIG. 15A, right panel).

Figure 15:
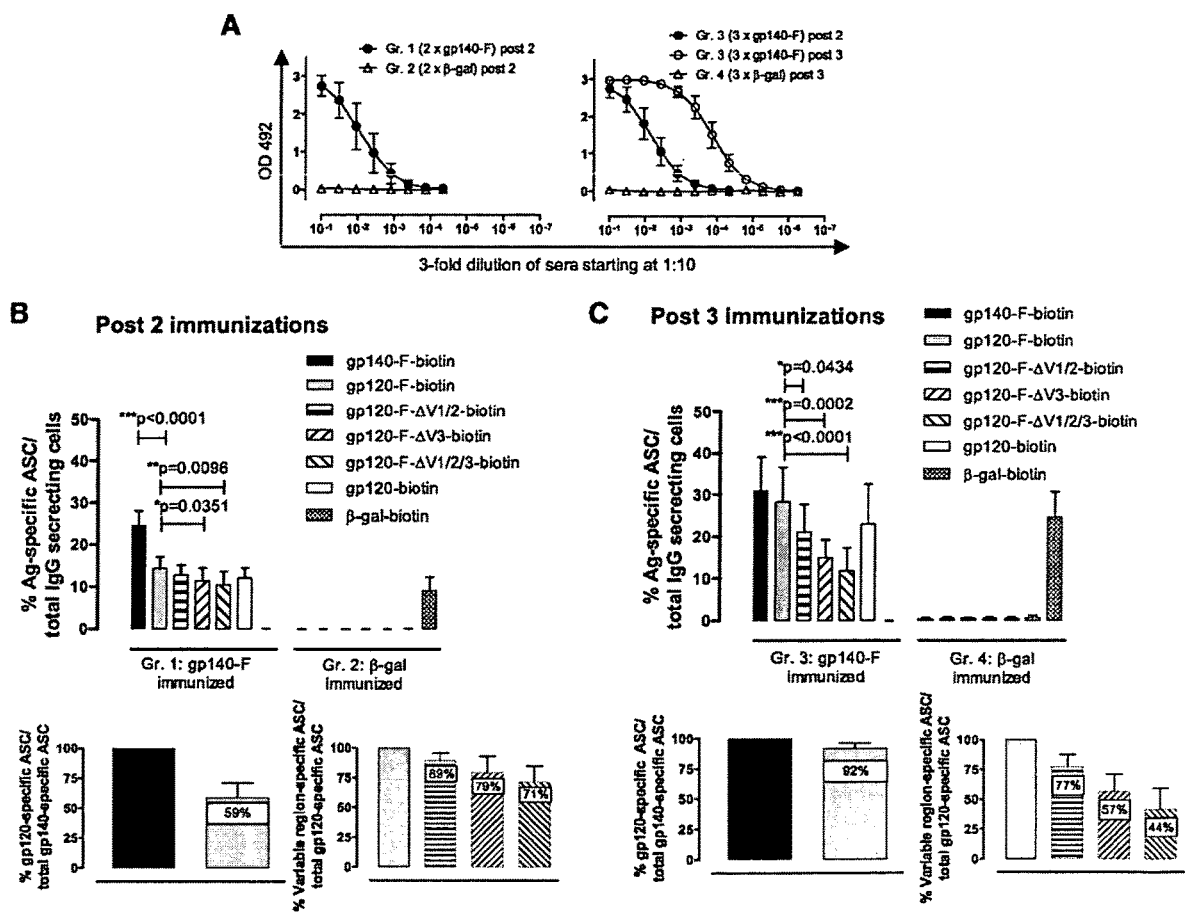
FIG. 15 shows differential B cell ELISPOT analysis of splenocytes from mice immunized two or three times with 140-F. A, Sera from mice immunized twice (group 1; left panel) or three times (group 3; right panel) with gp140-F were analyzed for Env-specific IgG in sera at day 3 after the second and third immunizations. Control mice were immunized twice (group 2; left panel) or three times (group 4; right panel) with n-gal. B, Env-specific ASC calculated as percentage of total IgG-secreting cells are shown for groups 1 and 2. The differential Env-specific B cell ELISPOT assay was used to examine the specificities of the Env-specific B cells (upper panel). In the lower panels, the data are shown as percentage of ASC recognized by the different probes compared with the total response to gp140-F-biotin (lower left panel) and gp120-F-biotin (lower right panel). C, The same diagrams and calculations as in B are shown for mice immunized three times with gp140-F (group 3) and β-gal (group 4). All graphs show mean values with SD, n=10 (gp140-F) and n=5 (β-gal). Statistical analysis was determined by Student's t test.

The frequencies of ASC reactive against selected structural Env elements were next determined using the differential B cell ELISPOT assay. About 25% gp140-F-specific ASC of total IgG-secreting cells after two immunizations and close to 30% after three immunizations (FIGS. 15, B and C). A significant fraction of the response post 2 immunizations was gp41 specific, as detected by comparing the percentage of gp120-F-specific spots with the percentage of gp140-F-specific spots (p<0.0001). Significant differences were also detected with the gp120-F-ΔV1/2/3 and gp120-F-ΔV3 probes compared with the gp120-F probe (p=0.0096 and p=0.0351, respectively) (FIG. 15B, upper panel).

When the percentage of gp140-F-specific ASC was normalized to 100%, 59% of the response was detected with the gp120-F probe, suggesting that the remaining 41% was gp41 specific (FIG. 15B, lower left panel). Similarly, when the gp120-F-specific response was normalized to 100%, the response detected with the 120-F-ΔV1/2/3 probe amounted to 71%, suggesting that 29% of the gp120-specific response was directed against V regions 1-3. The majority of these were directed against V3, as shown by using the gp120-F-ΔV3 probe (FIG. 15B, lower right panel). As expected, the β-gal-immunized mice showed a response with the β-gal probe, but not with the Env probes.

When the post 3 immunization samples were analyzed, a different pattern of responses was observed. The dominant response after three immunizations was directed against the V regions of gp120 (FIG. 15C). The percentages of ASC detected with the gp120-F-ΔV1/2/3, gp120-F-ΔV3, and gp120-F-ΔV1/2 probes were all significantly lower than those detected with gp120-F (p<0.0001, p=0.0002, and p=0.0434, respectively) In contrast, the fraction of ASC directed against gp41 was no longer significant (FIG. 15C, upper panel).

When the gp120-F-specific response was normalized to 100%, about 56% of the total gp120-specific response was directed against V regions 1-3, and the majority of this response was directed against V3 (FIG. 15C, lower right panel). There was no significant difference between the percentage of ASC detected with the gp120-F trimeric and the gp120 monomeric probes, suggesting that the stable gp140-F trimers used for immunization did not stimulate a detectable number of trimer-specific B cells.

Taken together, these results demonstrated that the gp41-specific response, which dominated after two immunizations, was not boosted by the third immunization. Instead, the third immunization resulted in an expansion of B cells specific for the V regions of gp120, consistent with the reported V3- and V1-directed neutralizing responses elicited by trimers and monomers, respectively.

Example 9

Having characterized the population of Env-specific ASC present in spleen 3 days after gp140-F trimer immunizations, how the response would evolve over time in the spleen compared with the bone marrow was studied. Mice were immunized twice or three times with gp140-F in adjuvant. The spleen and bone marrow were harvested 3 days after the second (group 1) and third (group 3) immunizations, and 21 days after the second (group 2) and third (group 4) immunizations for analysis using the differential B cell ELISPOT assay.

Figure 16:
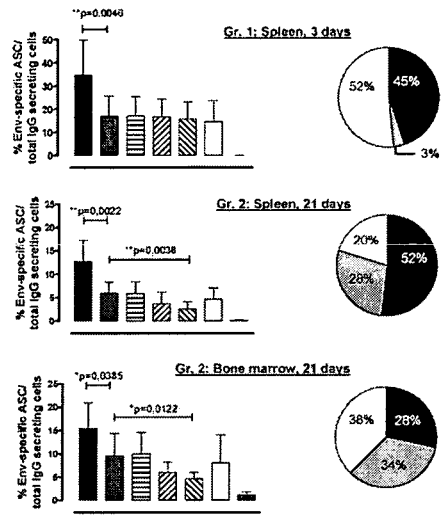
FIG. 16 shows Env-specific ASC in spleen and BM at days 3 and 21 after immunization. Upper panels, Differential B cell ELISPOT analysis of Env-specific ASC in spleen (days 3 and 21) and in bone marrow (day 21) after two immunizations. Lower panels, Differential B cell ELISPOT analysis of Env-specific ASC in spleen and BM (days 3 and 21) after three immunizations. Bar diagrams to the left show mean values of the percentage of probe-specific ASC of total IgG-secreting cells with SD, n=7-10. Statistical analysis was determined by Student's t test. Pie charts to the right show the percentage of ASC directed against gp41, V regions, or other 140-F specificities calculated from the same data as shown in the bar diagrams.
Figure 16:
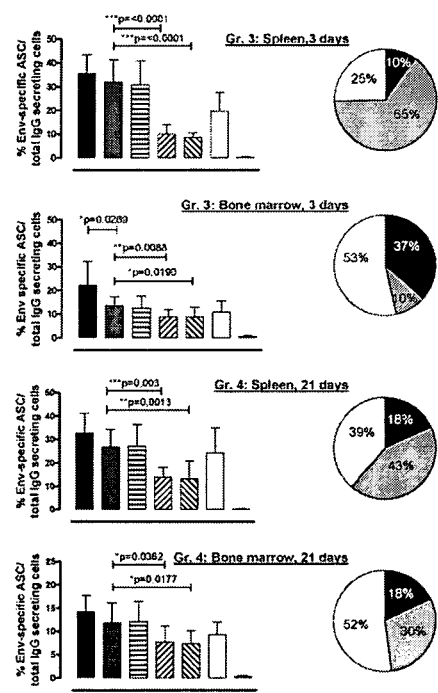

The results in FIG. 16 are shown in two ways, as follows: bar diagrams on the left represent percentage of Env-specific ASC of total IgG-secreting cells as detected with the different probes, and the pie charts on the right show percentage of reactivity against gp41 (calculated as the differential between the gp140-F and the gp120-F probe) and percentage of reactivity against V regions 1-3 (calculated as the differential between the 140-F and the 120-F-ΔV1/2/3 probe after the gp41 reactivity was subtracted). The analyses of splenocytes harvested 3 days after immunization were consistent with the results shown in FIG. 16. In group 1, there was a significant difference in the percentage of ASC detected with the gp140-F probe compared with the gp120-F probe (p=0.0046), whereas no significant difference between these probes was detected after the third immunization. As previously observed, the V3-directed responses dominated after three immunizations (group 3) in a statistically significant manner (p<0.0001 for the V3 region differential), whereas the differential between the gp120-F and gp120-F-ΔV1/2 probes was not significant at either time point.

When the ASC were enumerated 21 days after the second immunization (group 2), a significant fraction was directed against the V regions (p=0.0038), suggesting selective expansion of these cells over time. Furthermore, a significant fraction (p=0.0122) of V region-directed ASC was also measured in the BM 21 days after the second immunization. When responses in bone marrow were measured 3 days (group 3) and 21 days (group 4) after the third immunization, a significant fraction of gp41-directed ASC was observed at day 3, but not at day 21. This difference may be explained by the time required for ASC expansion and redistribution to the bone marrow following the third immunization. The relative frequencies of Env-specific ASC in the BM measured 21 days after both the second and the third immunization were qualitatively similar to those measured in the spleen at the same time point, except that the fraction of non-gp41, non-V region-directed ASC was higher in the bone marrow at both time points, as illustrated by the pie charts. The V region-directed ASC in the pie charts were primarily represented by V3-directed responses, as shown by the bar diagrams.

In many instances, it is of interest to characterize the memory B cell response induced by candidate vaccines. Unlike plasma cells, memory B cells do not spontaneously secrete antibodies, but can be stimulated to do so in vivo by re-exposure to antigen, or, in vitro, if cultured in the presence of antigenic or polyclonal stimulators that promote their expansion and differentiation into ASC. An advantage of the B cell ELISPOT analysis over serological analysis is that B cell ELISPOT approach allows an examination of the memory B cell compartment also. The differential B cell ELISPOT assay was employed to measure Env-specific memory B cells by culturing splenocytes collected 21 days after two or three immunizations with gp140-F trimers in LPS to expand and differentiate memory B cells to ASC. This analysis demonstrates that the specificities present in the total ASC population were reflected in the memory B cell pool.

Finally, whether the probes developed for the differential B cell ELISPOT assay described in this work could be used in ELISA for differential detection of antibodies in sera was studied. The gp120-F and gp120-F-ΔV1/2/3 probes and performed ELISA on sera taken 21 days after three immunizations with 140-F were selected.

Figure 17:
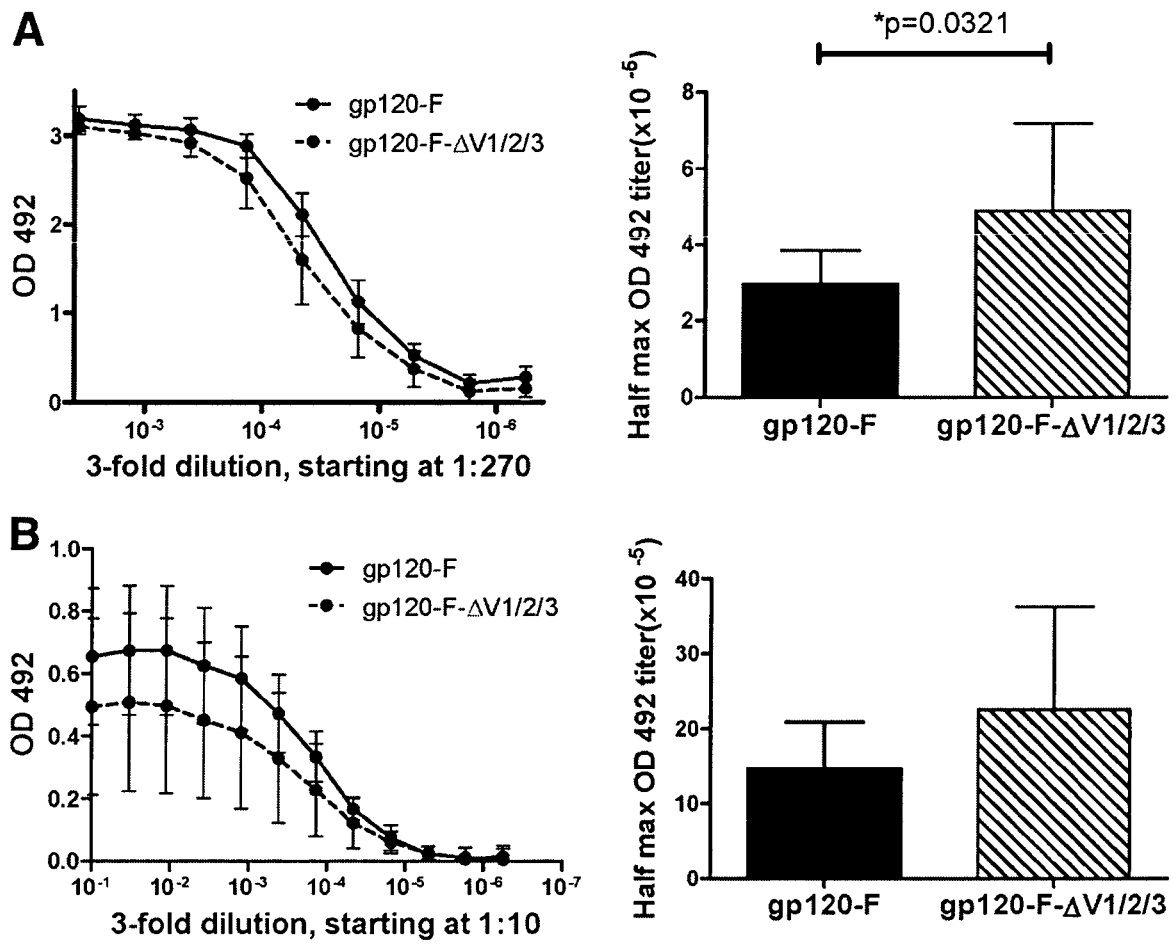
FIG. 17 shows differential ELISA of Env-specific Abs in sera. A, ELISA was run with protein coated to the wells by using both gp120-F (solid line) and 120-F-Δ1/2/3 (dotted line) for detection of Env-specific Abs. Left panel, Titration curves of the sera in 3-fold serial dilutions, starting at 1:270; right panel, half-maximum OD values of the ELISA curves. B, ELISA was run in a similar format as the optimized Ag-specific B cell ELISPOT, with wells coated with a polyclonal anti-mouse IgG and detection of Env-specific Abs by the addition of gp120-F-biotin (solid line) and gp120-F-Δ1/2/3-biotin (dotted line). Left panel, Titration curves of sera in 3-fold serial dilutions starting at 1/10. Right panel, Half-maximum OD values of the ELISA curves. Sera from mice immunized three times with 140-F, taken day 21 after the last immunization, were used in the analysis. Graphs show mean values with SD, n=8-9. Statistical analysis was determined by Student's t test.

The analysis was performed using two different formats, as follows: a standard ELISA in which the proteins were used for coating (FIG. 17A), and an ELISA that mimics the format of the optimized B cell ELISPOT assay, i.e., by coating the ELISA wells with anti-IgG and probing with biotinylated proteins (FIG. 17B). In the former ELISA format, a difference was detected between the two antigens, indicating a concordance between B cell ELISPOT responses and the serological responses.

for the antigens indicates that the subject has previously been exposed to the antigens.

8. The method according to claim 1, where the plurality of different antigens are from a plurality of pathogens, allowing which pathogen is infecting the subject to be determined.

The invention claimed is:

1. A method of detecting antibody secreting cells specific for an antigen in a sample from a subject, the method comprising:
   (a) providing:
      (i) a sample comprising antibody secreting cells;
      (ii) a surface on which anti-Ig antibodies are immobilized, wherein the surface is the base of a well; and
      (iii) a plurality of different antigens from different infectious pathogens, tumour antigens, autoimmune proteins or allergens, which are each differently fluorescently labelled;
   (b) contacting the sample and the surface under conditions suitable for antibodies produced by the antibody secreting cells to bind to the immobilised anti-Ig antibodies on the surface;
   (c) removing the antibody secreting cells by washing;
   (d) contacting the surface with the plurality of differently fluorescently labelled antigens under conditions suitable for the differently labelled antigens to bind to antibodies specific for the antigens; and
   (e) detecting any labelled antigens captured on the surface through the presence of fluorescent signals produced by said labelled antigens, wherein the detectable fluorescent signals are present as spots on the surface.

2. The method according to claim 1, where the method further comprises determining the number of spots via fluorescence.

3. The method according to claim 1, wherein the sample is a sample of peripheral blood mononuclear cells.

4. The method according to claim 1, wherein the subject has potentially been exposed to an infectious agent but does not show any signs of infection.

5. The method according to claim 4, wherein the infectious agent is HIV.

6. The method according to claim 5, wherein at least one of the plurality of different antigens is an envelope glycoprotein.

7. The method according to claim 1, wherein the subject has serum/plasma antibodies to at least one of the antigens and the presence of antibody-secreting cells specific for the at least one antigen indicates that the subject has acute infection or the absence of antibody-secreting cells specific 9. A kit for detecting or measuring Antibody Secreting Cells (ASCs) producing antibodies against a plurality of different antigens from different infectious pathogens, tumour antigens, autoimmune proteins or allergens, which kit comprises:
   (i) a surface on which anti-Ig antibodies are immobilised, wherein the surface is the base of a well; and
   (ii) said plurality of different antigens from different infectious
   pathogens, tumour antigens, autoimmune proteins or allergens, where each is differently fluorescently labelled.

10. A method of detecting antibody secreting cells specific for an antigen in a sample from the subject, the method comprising:
   (a) providing:
      (i) a sample comprising antibody secreting cells;
      (ii) a surface on which anti-Ig antibodies are immobilized, wherein the surface is the base of a well; and
      (iii) a plurality of different antigens from different infectious pathogens, tumour antigens, autoimmune proteins or allergens, which are each differently labelled, where each different label is detectable via a different colour fluorochrome;
   (b) contacting the sample and the surface under conditions suitable for antibodies produced by the antibody secreting cells to bind to the immobilised anti-Ig antibodies on the;
   (c) removing the antibody secreting cells by washing;
   (d) contacting the surface with the plurality of differently labelled antigens under conditions suitable for the differently labelled antigens to bind to antibodies specific for the antigens; and
   (e) detecting any labelled antigen captured on the surface through the presence of fluorescent signals produced by said labelled antigens, where each different label is detected via a different colour fluorochrome, where the detectable fluorescent signals are present as differently coloured spots on the surface.

11. The method according to claim 10, where at least one of the antigens is a HIV antigen.

12. The method of claim 1, wherein the antigens comprises three or four different antigens.

13. The method of claim 1, wherein the sample comprises B cells purified from peripheral blood mononuclear cells.

14. The method of claim 1, where the different antigens are from a plurality of pathogens which are different strains of the same pathogen and the different antigens are variant forms of the same antigen.

15. The method of claim 1, wherein the subject is a child.

16. The kit of claim 9, wherein the plurality of antigens comprises three or more different antigens.

17. The kit of claim 9, where the plurality of different antigens are from a plurality of pathogens which are different strains of the same pathogen and the different antigens are variant forms of the same antigen.

18. The method of claim 10, wherein the antigens comprises three different antigens.

19. The method of claim 10, wherein the sample comprises B cells purified from peripheral blood mononuclear cells.

20. The method of claim 10, where the plurality of different antigens are from a plurality of pathogens which are different strains of the same pathogen and the different antigens are variant forms of the same antigen.

21. The method of claim 10, wherein the subject is a child.

22. The method of claim 1, wherein the plurality of different antigens from different infectious pathogens, tumour antigens, autoimmune proteins or allergens, are each differently labelled with differently coloured fluorescent labels.

23. The kit of claim 9, wherein the plurality of different antigens from different infectious pathogens, tumour antigens, autoimmune proteins or allergens, are each differently labelled with differently coloured labels.

24. The method of claim 10, wherein said plurality of differently labelled antigens comprise three, four five or six different antigens from different infectious pathogens, tumour antigens, autoimmune proteins or allergens which each differently fluorescently labelled with differently coloured fluorochromes.

* * * * *

SEQUENCE LISTING

```
<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: Avitaq signal for biotinylation

<400> SEQUENCE: 1

Gly Leu Asn Asp Ile Phe Glu Ala Gln Lys Ile Glu Trp His Glu
1               5                   10                  15
```

UNITED STATES PATENT AND TRADEMARK OFFICE
CERTIFICATE OF CORRECTION

PATENT NO. : 10,564,160 B2
APPLICATION NO. : 13/061085
DATED : February 18, 2020
INVENTOR(S) : Pia Dosenovic et al.

Page 1 of 1

It is certified that error appears in the above-identified patent and that said Letters Patent is hereby corrected as shown below:

In the Claims

Column 40, Line 52, Claim 10 replace "on the;" with --on the surface--.

Column 42, Line 14, Claim 24 replace "comprise three, four five or six" with --comprise three, four, five, or six--.

Signed and Sealed this
Fourteenth Day of April, 2020

Andrei Iancu
*Director of the United States Patent and Trademark Office*